(12) United States Patent
Kanamune et al.

(10) Patent No.: US 8,852,934 B2
(45) Date of Patent: Oct. 7, 2014

(54) METHOD OF CULTURING PANCREATIC ISLET-LIKE TISSUES BY A TISSUE COMPLEX OF PANCREAS-DERIVED NON-ENDOCRINAL EPITHELIAL CELLS AND VASCULAR ENDOTHELIAL CELLS

(75) Inventors: Jun Kanamune, Kyoto (JP); Yasuhiro Iwanaga, Kyoto (JP); Shinji Uemoto, Kyoto (JP); Yoshiya Kawaguchi, Kyoto (JP)

(73) Assignee: Kyoto University, Kyoto-shi (JP)

( * ) Notice: Subject to any disclaimer, the term of this patent is extended or adjusted under 35 U.S.C. 154(b) by 0 days.

(21) Appl. No.: 13/635,630

(22) PCT Filed: Mar. 15, 2011

(86) PCT No.: PCT/JP2011/001519
§ 371 (c)(1),
(2), (4) Date: Sep. 17, 2012

(87) PCT Pub. No.: WO2011/114719
PCT Pub. Date: Sep. 22, 2011

(65) Prior Publication Data
US 2013/0122586 A1    May 16, 2013

(30) Foreign Application Priority Data
Mar. 17, 2010    (JP) .................................. 2010-061404

(51) Int. Cl.
*C12N 5/071*    (2010.01)
*C12N 5/00*    (2006.01)

(52) U.S. Cl.
CPC .......... *C12N 5/0677* (2013.01); *C12N 2502/28* (2013.01); *C12N 5/0676* (2013.01)
USPC ............................ 435/366; 435/373; 435/395

(58) Field of Classification Search
None
See application file for complete search history.

(56) References Cited

U.S. PATENT DOCUMENTS 6,815,203 B1 * 11/2004 Bonner-Weir et al. ........ 435/377
2005/0048040 A1    3/2005 Powers et al.
2006/0246582 A1 * 11/2006 Navran, Jr. .................... 435/366

FOREIGN PATENT DOCUMENTS

WO    2008/063640 A2    5/2008

OTHER PUBLICATIONS

Johansson et al., Endocrinology 147: 2315-2324 (2006).*
Nikolova et al., Trends in Cell Biol. 17(1): 19-25 (2006).*
Nakamura et al., Biochem. Biophys. Res. Comm. 350: 68-73 (2006).*
McEvoy et al., Diabetes 28: 141-146.*
Cras-Meneur et al., Genes Dev. 23: 2088-2101 (2009).*

(Continued)

*Primary Examiner* — Patricia A Leith
*Assistant Examiner* — Erin M Bowers
(74) *Attorney, Agent, or Firm* — Westerman, Hattori, Daniels & Adrian, LLP

(57) ABSTRACT

According to embodiments, a method of producing insulin-producing tissues (IPTs) by culturing comprises: preparing non-endocrinal epithelial cells (NEECs) and vascular endothelial cells (VECs), which have been isolated or originated from postnatal pancreata, preferably by capturing of NEECs by collagen; culturing in vitro the NEECs and the VECs at least partly separately from each other; and then generating in vitro a tissue complex (IPTs) that contains both the NEECs and the VECs. In another embodiment, the native islet cells are seeded on a monolayer of VECs that have preferably been separately cultured and purified. In a further embodiment, a method of enriching NEECs comprises: culturing NEECs adhering to a container or substrate; removing NEECs by treating with a tissue-dissociation enzyme to leave left-over cells (LOCs) still attached on the container or substrate; and culturing NEECs in a medium conditioned by, or in the presence of the LOCs.

19 Claims, 17 Drawing Sheets

(56) References Cited

OTHER PUBLICATIONS

Chen et al., Stroke 39(1): 220-226 (2008).*
Thermo Electron Corporation, "Accutase Cell Detachment Solution", 2005.*
Todorov et al., Pancreas 32(2): 130-138 (2006).*
Ogata et al., Endocrine J. 51(3): 381-386 (2004).*
Suckale et al., Frontiers in Bioscience 13: 7156-7171 (2008).*
Goulley et al., Cell Metab. 5: 207-219 (2007).*
Lechner et al., Biochem. Biophys. Res. Comm. 327: 581-588 (2005).*
Xu et al., "β Cells Can Be Generated from Endogenous Progenitors in Injured Adult Mouse Pancreas", Cell, dated Jan. 25, 2008, vol. 132, p. 197-207.
Chen et al., "Atorvastatin Promotes Presenilin-1 Expression and Notch1 Activity and Increases Neural Progenitor Cell Proliferation After Stroke", Stroke, dated Jan. 2008, p. 220-226.
Kanamune et al., "Swirl Differentiation of Murine Pancreatic Non-endocrinal Epithelial Cells into Insulin-secreting Cells", Regenerative Medicine, dated 2009, vol. 8, No. 31, p. 154, O-12-4. With English Translation. (Title alternatively translated as: "Development of a gyratory differentiation method of Insulin-secreting cells using mouse pancreas-derived non-endocrinal epithelial cells.").
Limbert, C. et al., "Beta-cell replacement and regeneration: Strategies of cell-based therapy for type 1 diabetes mellitus", Diabetes Research and Clinical Practice, 2008, vol. 79, pp. 389-399, Extended European Search Report dated Nov. 7, 2013.
Hao, Ergeng et al., "Beta-cell differentiation from nonendocrine epithelial cells of the adult human pancreas", Nature Medicine, 2006, pp. 1-7, Extended European Search Report dated Nov. 7, 2013.
Bonner-Weir, Susan et al., "Transdifferentiation of pancreatic ductal cells to endocrine b-cells", Biochem. Soc. Trans., 2008, vol. 36, pp. 353-356, Extended European Search Report dated Nov. 7, 2013.
Extended European Search Report dated Nov. 7, 2013, issued in corresponding European application No. 11755910.4.
Xu et al., "βCells Can Be Generated from Endogenous Progenitors in Injured Adult Mouse Pancreas", Cell, dated Jan. 25, 2008, vol. 132, p. 197-207.
Rovira et al., "Isolation and characterization of centroacinar/terminal ductal progenitor cells in adult mouse pancreas", PNAS, dated Jan. 5, 2010, vol. 107, No. 1, p. 75-80.
Crivellato et al., "Contribution of endothelial cells to organogenesis: a modern reappraisal of an old Aristotelian concept", J. Anat., dated 2007, vol. 211, p. 415-427.
Todorov, et al., "Generation of Human Islets Through Expansion and Differentiation of Non-islet Pancreatic Cells Discarded (Pancreatic Discard) After Islet Isolation", Pancreas, dated Mar. 2006, vol. 32, No. 2, p. 130-138.
Bonner-Weir et al., "In vitro cultivation of human islets from expanded ductal tissue", PNAS, dated Jul. 5, 2000, vol. 97, No. 14, p. 7999-8004.
Katdare et al., "Analysis of morphological and functional maturation of neoislets generated in vitro from pancreatic ductal cells and their suitability for islet banking and transplantation", Journal of Endocrinology, dated 2004, vol. 182, p. 105-112.

Suzuki et al., "Prospective Isolation of Multipotent Pancreatic Progenitors Using Flow-Cytometric Cell Sorting", Diabetes, dated Aug. 2004, vol. 53, p. 2143-2152.
Seaberg et al., "Clonal identification of multipotent precursors from adult mouse pancreas that generate neural and pancreatic lineages", Nature Biotechnology, dated Aug. 22, 2004, vol. 22, No. 9, p. 1115-1124.
Conboy et al., "Notch-Mediated Restoration of Regenerative Potential to Aged Muscle", Science, dated Nov. 28, 2003, vol. 302, p. 1575-1577.
Cras-Meneur et al., "Presenilins, Notch dose control the fate of pancreatic endocrine progenitors during a narrow developmental window", Genes & Development, dated 2009, p. 2088-2101.
Chen et al., "Atorvastatin Promotes Presenilin-1 Expression and Notch1 Activity and Increases Neural Progenitor Cell Proliferation After Stroke", Stroke, dated Jan. 2008, p. 220-226.
Dor et al., "Adult pancreatic B-cells are formed by self-duplication rather than stem-cell differentiation", Nature, dated May 6, 2004, vol. 429, p. 41-46.
Inada et al., "Carbonic anhydrase II-positive pancreatic cells are progenitors for both endocrine and exocrine pancreas after birth", PNAS, dated Dec. 16, 2008, vol. 105, No. 50, p. 19915-19919.
Yoshitomi et al., "Endothelial cell interactions initiate dorsal pancreas development by selectively inducing the transcription factor Ptf1a", Development, dated 2004, vol. 131, p. 807-817.
Lammert, et al., "Induction of Pancreatic Differentiation by Signals from Blood Vessels", Science, dated Oct. 19, 2001, vol. 294, p. 564-567.
Nikolova et al., "The vascular niche and its basement membrane", Trends in Cell Biology, dated Nov. 28, 2006, vol. 17, No. 1, p. 19-25.
Cirulli et al., "Expression and Function of avb3 and avb5 Integrins in the Developing Pancreas: Roles in the Adhesion and Migration of Putative Endocrine Progenitor Cells", Journal of Cell Biology, dated Sep. 18, 2000, vol. 150, No. 6, p. 1445-1459.
Johansson et al., "Islet Endothelial Cells and Pancreatic B-Cell Proliferation: Studies in Vitro and during Pregnancy in Adult Rats", Endocrinology, dated 2006, vol. 147, p. 2315-2324.
Ogata et al., "Reversal of Streptozotocin-induced Hyperglycemia by Transplantation of Pseudoislets Consisting of B Cells Derived from Ductal Cells", Endocrine Journal, dated 2004, vol. 50, p. 381-386.
Xia et al., "Can pancreatic duct-derived progenitors be a source of islet regeneration?", Biochemical and Biophysical Research Communications, dated 2009, vol. 383, No. 4, p. 383-385.
Kanamune et al., "Swirl Differentiation of Murine Pancreatic Non-endocrinal Epithelial Cells into Insulin-secreting Cells", Regenerative Medicine, dated 2009, vol. 8, No. 31, p. 154, O-12-4. With English Translation.
Murray et al., "Sustained insulin secretory response in human islets co-cultured with pancreatic duct-derived epithelial cells within a rotational cell culture system", Diabetologia, dated 2009, vol. 52, No. 3, p. 477-485.
Kanamune et al., "Development of a novel selective culture method of Pancreatic islet-like tissues using Pancreatic Discard After Islet Isolation", Transplantation, dated Oct. 2010, vol. 45, No. 1, p. 228.
Ta, et al., "The Defined Combination of Growth Factors Controls Generation of Long-Term-Replicating Islet Progenitor-Like Cells from Cultures of Adult Mouse Pancreas", Stem Cells, dated 2006, vol. 24, p. 1738-1749.
International Search Report of PCT/JP2011/001519, dated Jun. 14, 2011.

* cited by examiner

Fig. 1-A
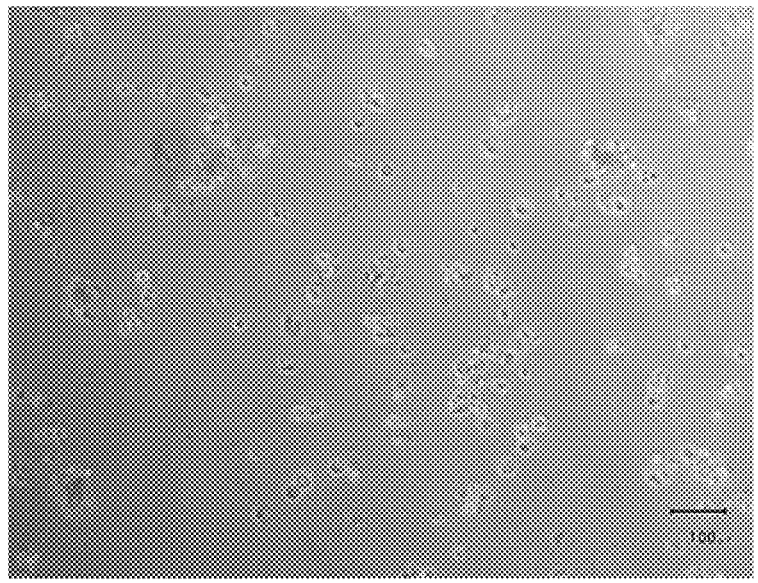
Fig. 1-B
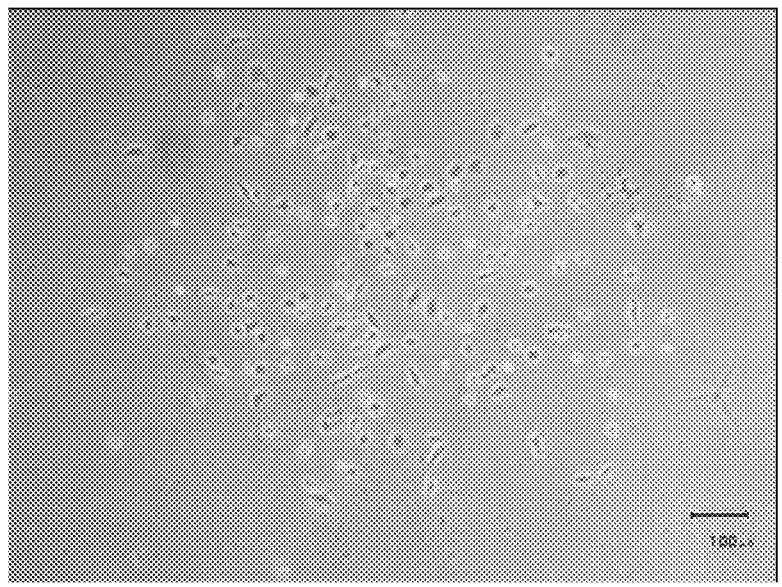

Fig. 1-C
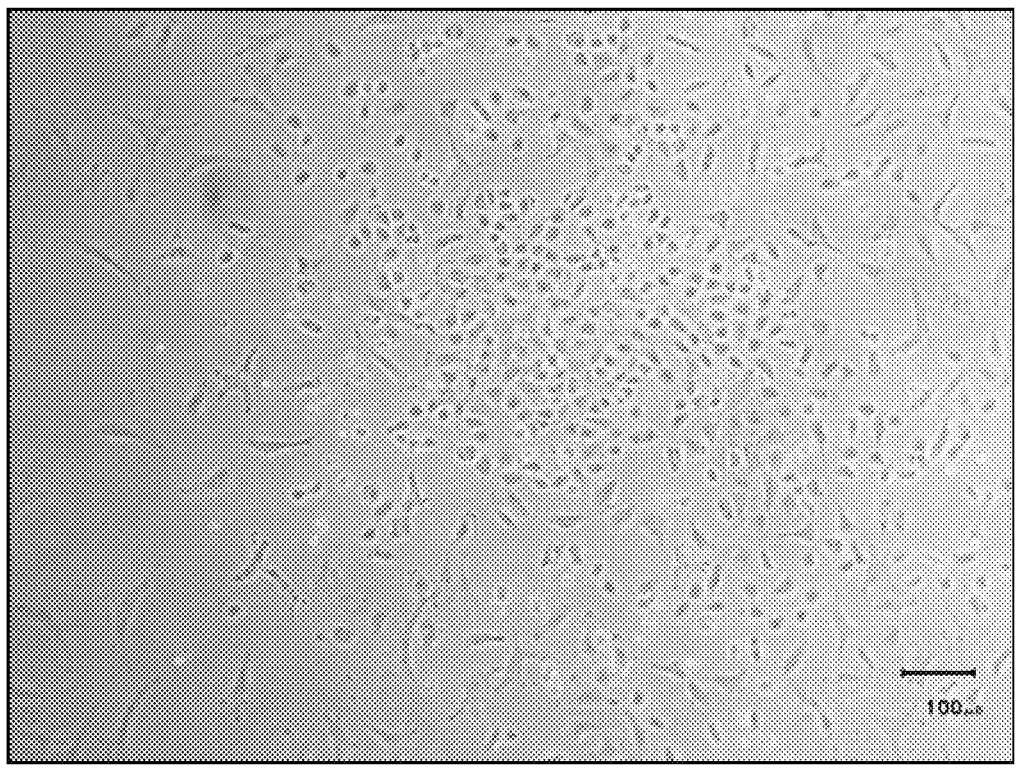
Fig. 1-D
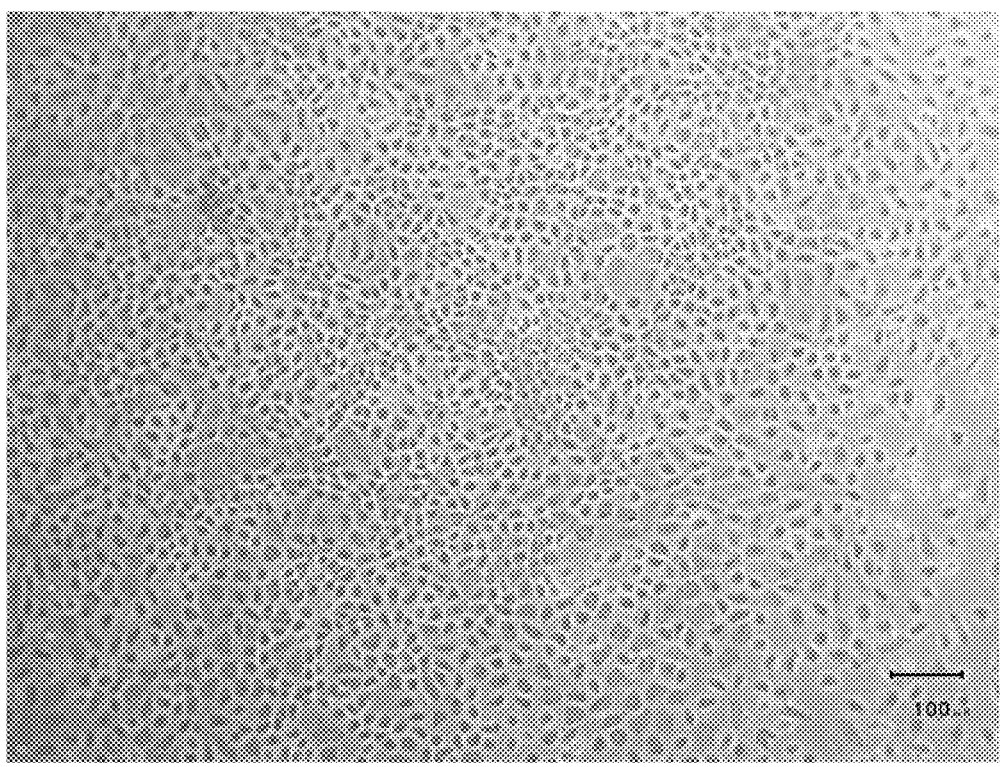

Fig. 2-A
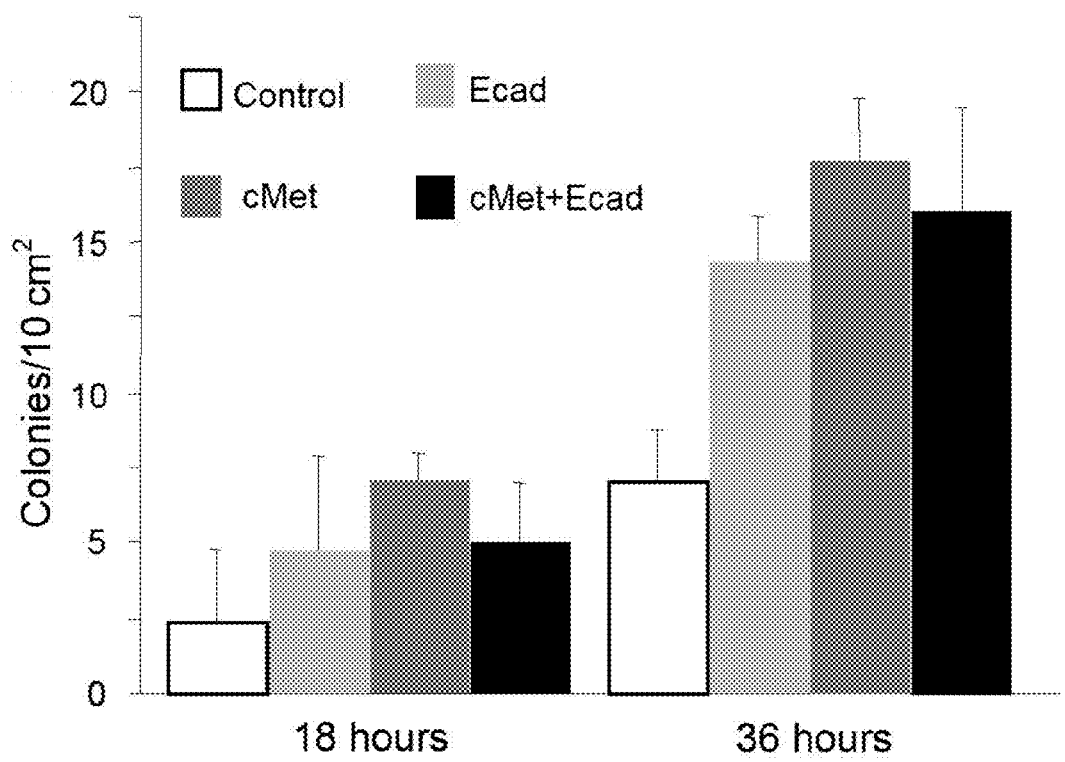
Fig. 2-B
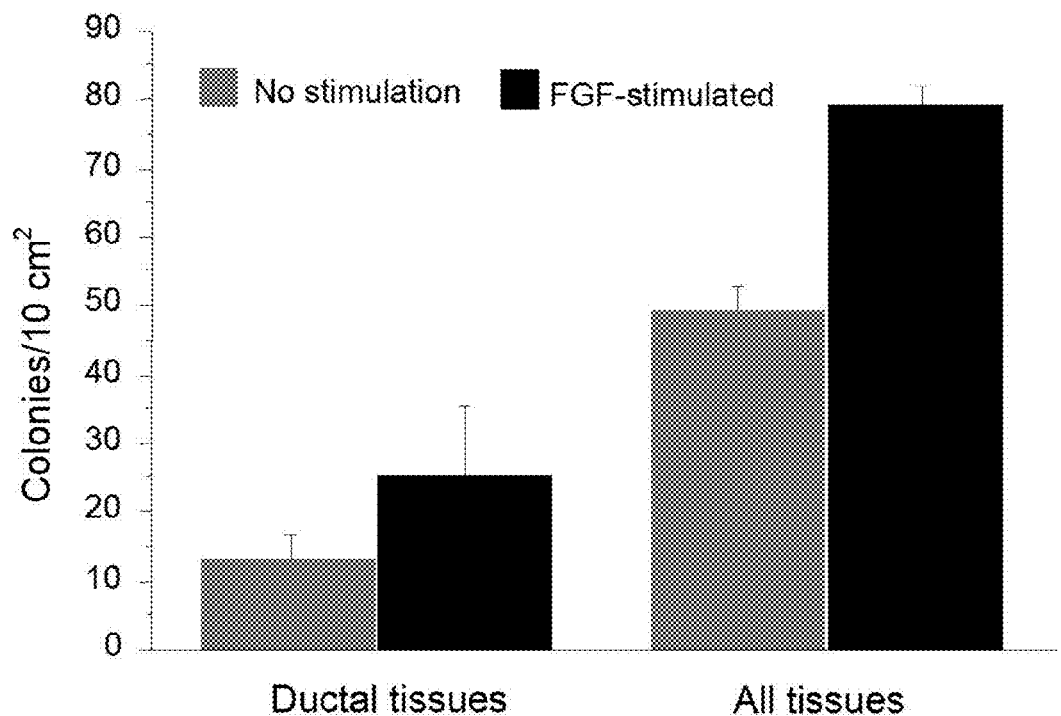

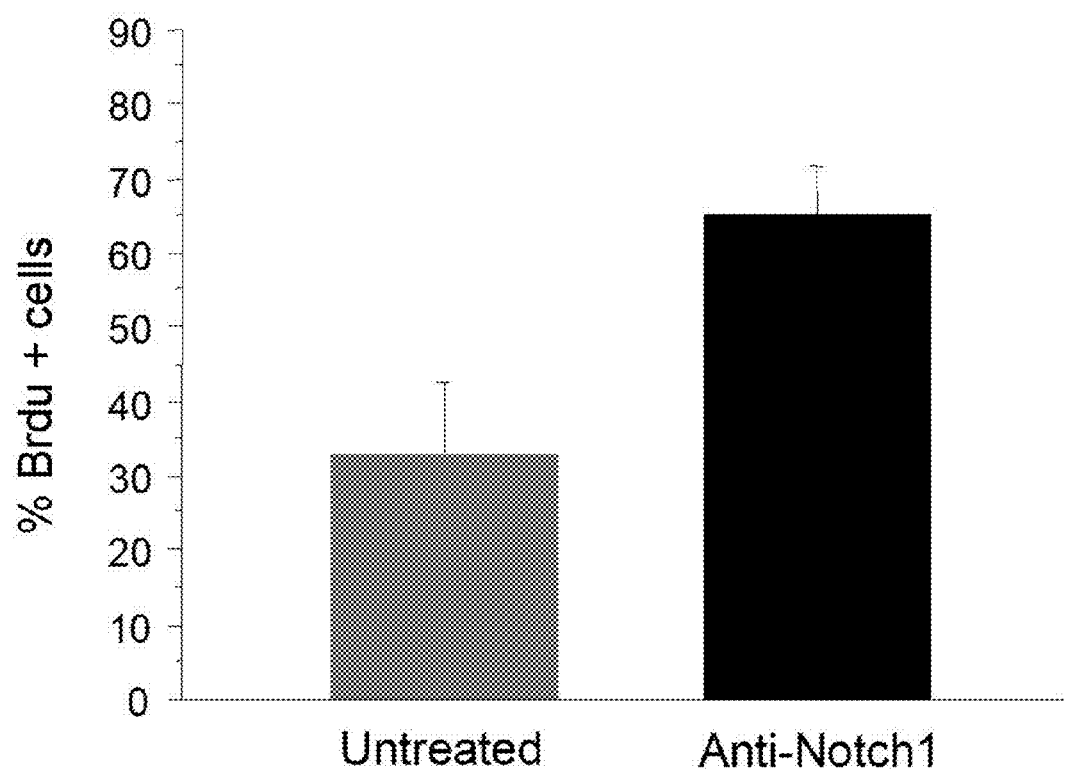
Fig. 2-C

Fig. 3-2
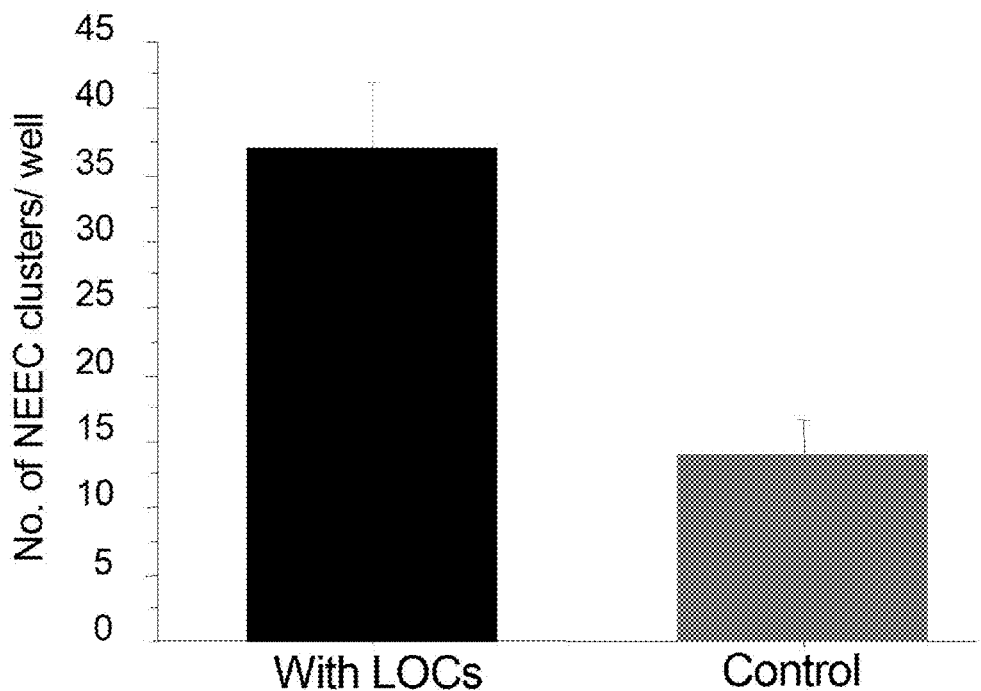
Fig. 3-3
*Pdx-1*
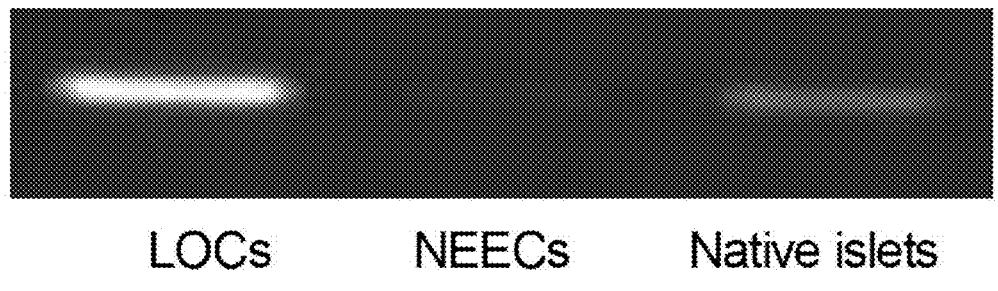
LOCs    NEECs    Native islets
*Ins1*
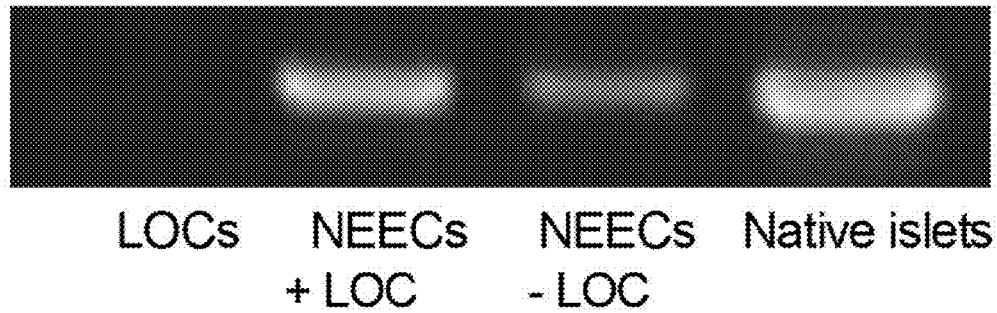
LOCs    NEECs    NEECs    Native islets
        + LOC    - LOC Fig. 4-A
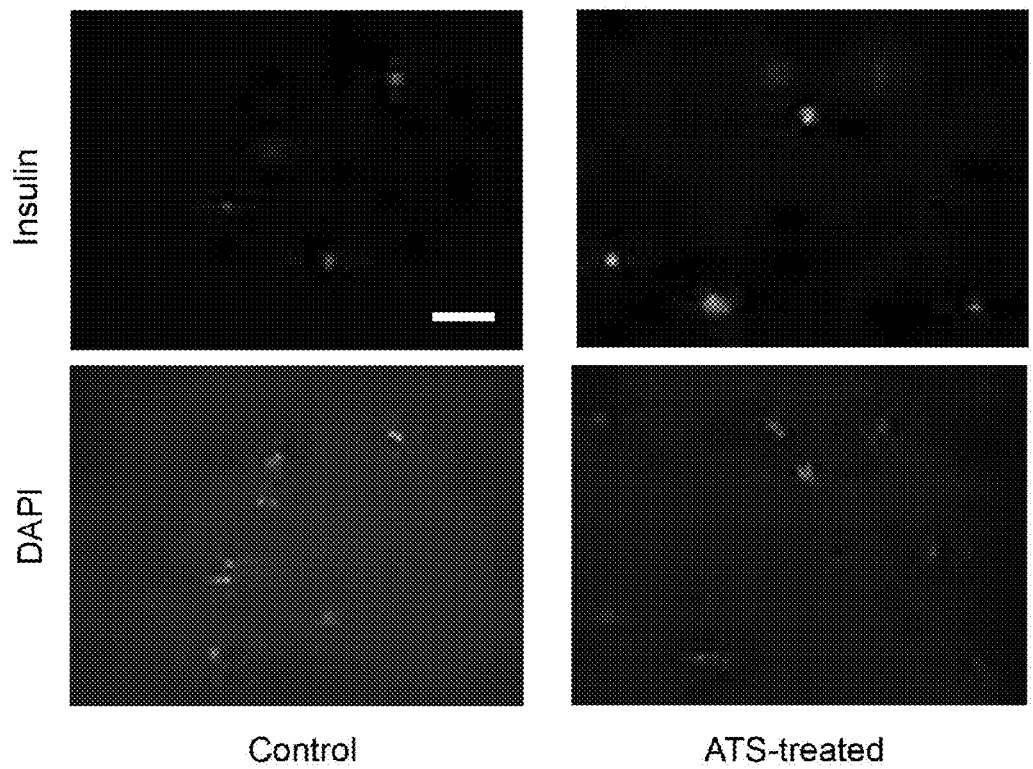
Fig. 4-B
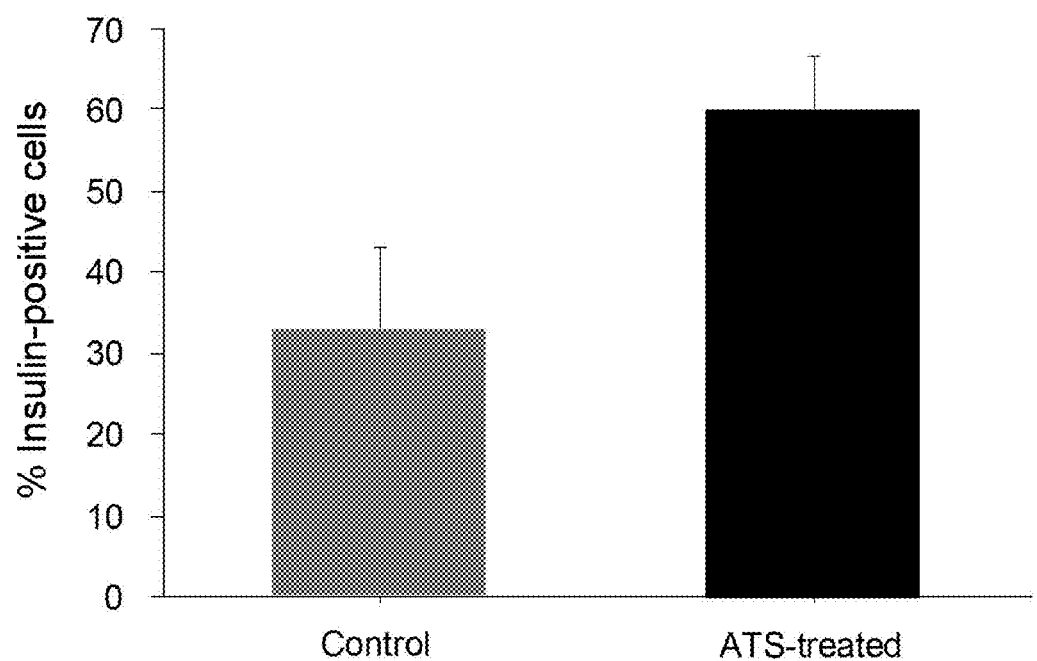

Fig. 5-A
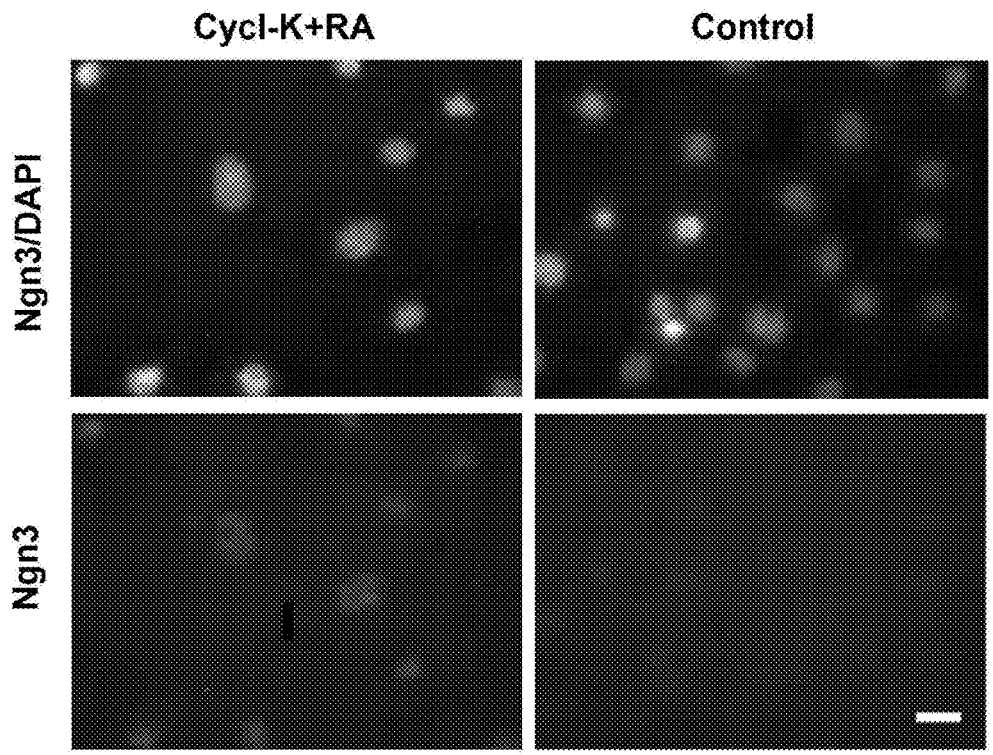
Fig. 5-B
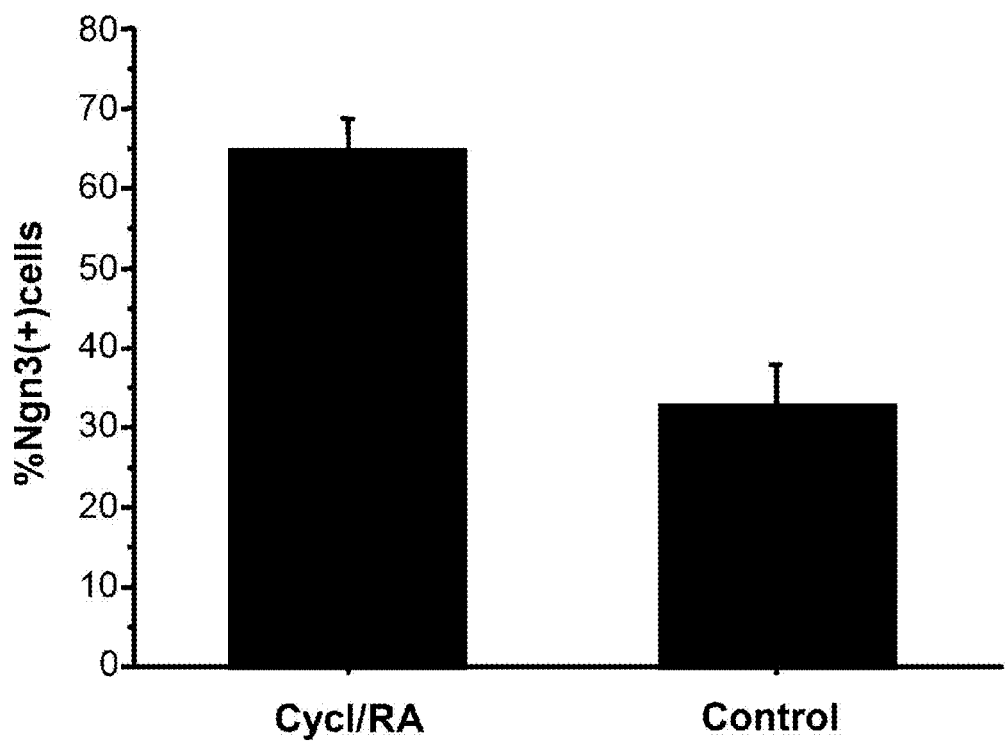

Fig. 6-A
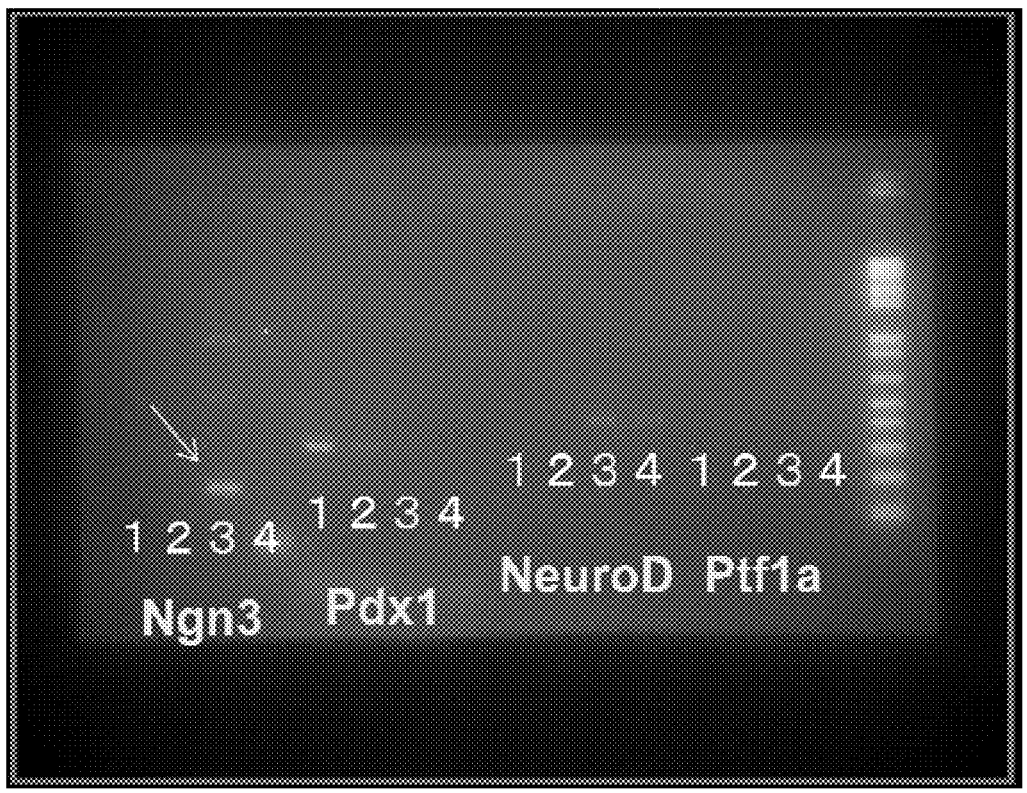
Fig. 6-B
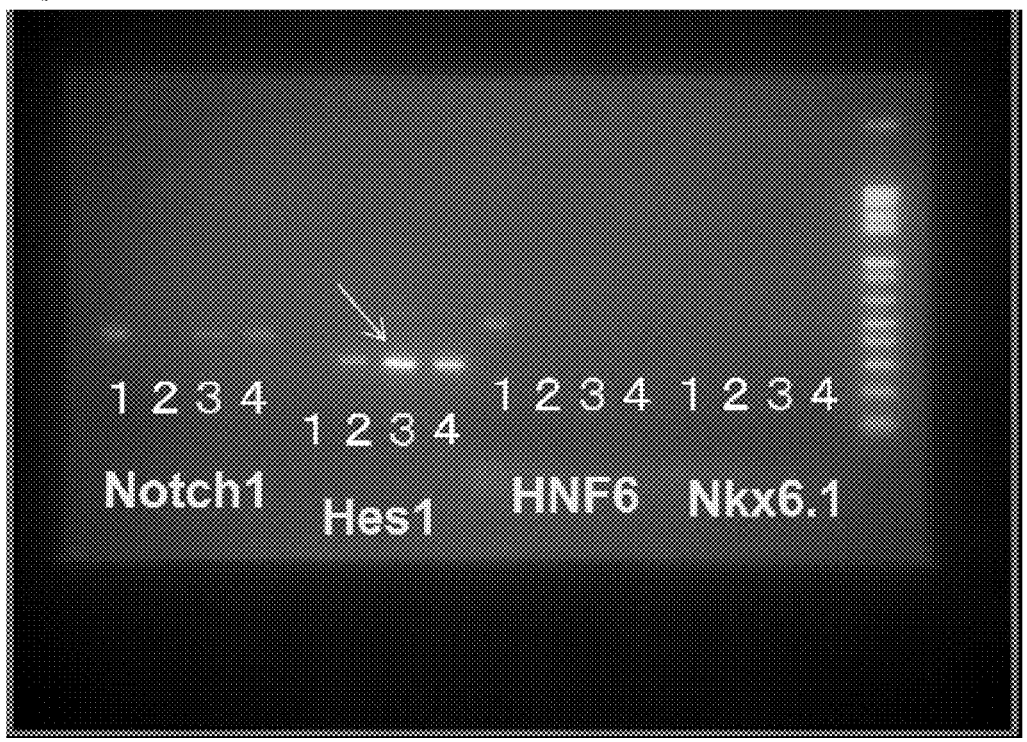

Fig. 9-A
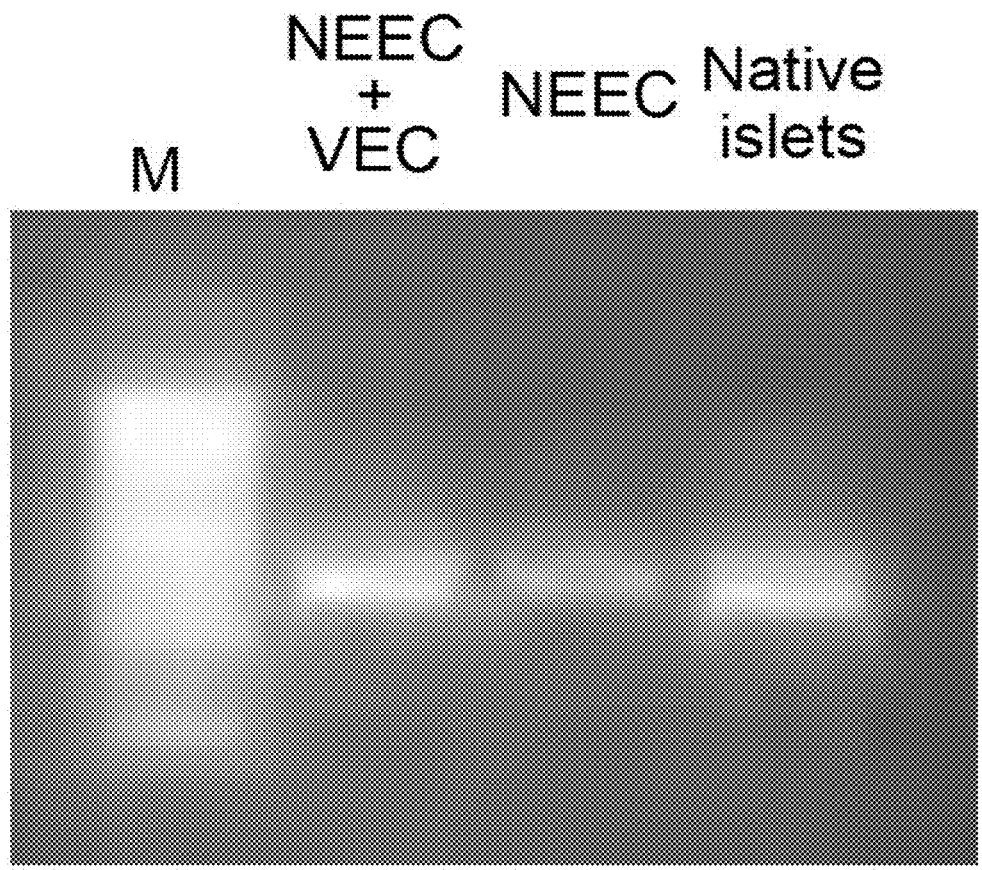
Fig. 9-B
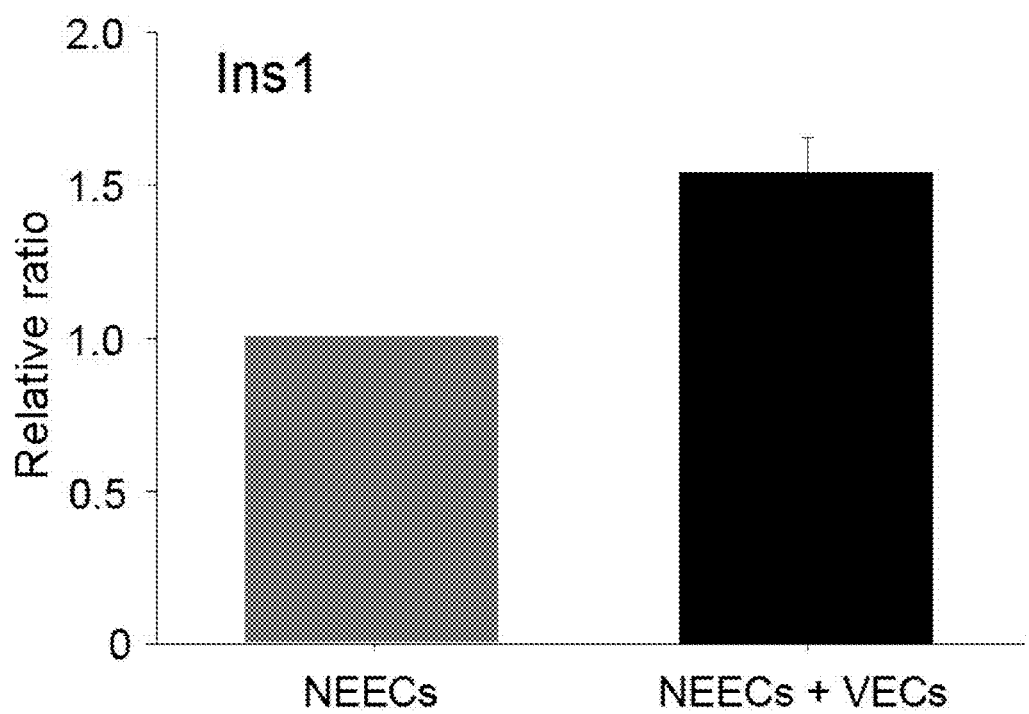

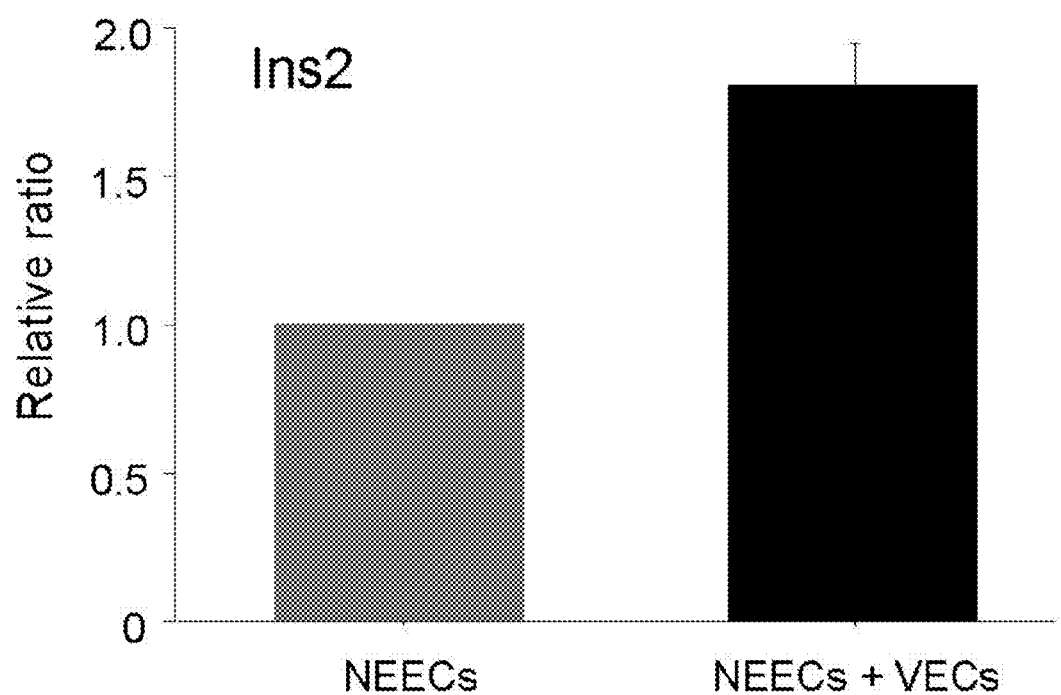

Fig. 10-A
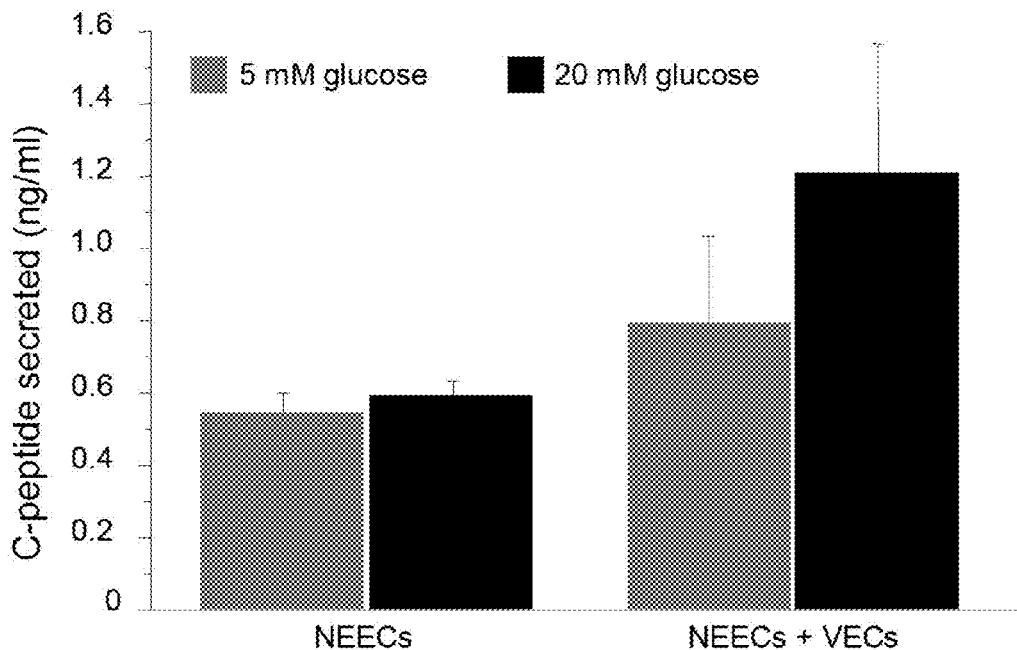
Fig. 10-B
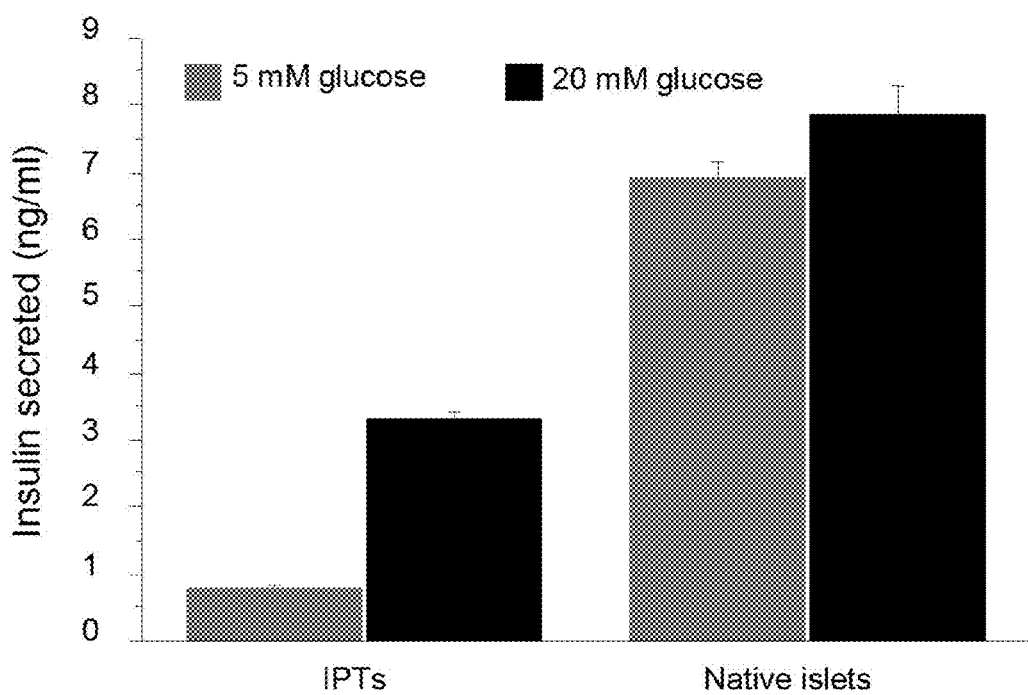

Fig. 12-A

Fig. 12-B
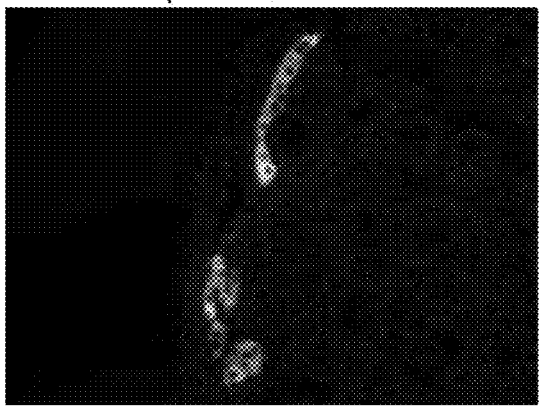
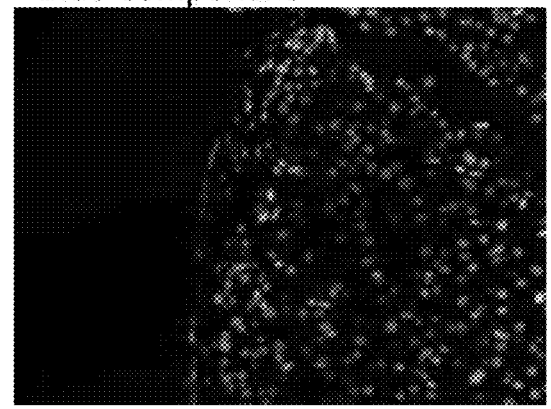

SEQUENCE LISTING

<160> NUMBER OF SEQ ID NOS: 22

<210> SEQ ID NO 1
<211> LENGTH: 20
<212> TYPE: DNA
<213> ORGANISM: Artificial Sequence
<220> FEATURE:
<221> NAME/KEY: Ngn3 (F)
<223> OTHER INFORMATION: Chemically synthesized primer

<400> SEQUENCE: 1
cagtcaccca cttctgcttc                                          20

<210> SEQ ID NO 2
<211> LENGTH: 20
<212> TYPE: DNA
<213> ORGANISM: Artificial Sequence
<220> FEATURE:
<221> NAME/KEY: Ngn3 (R)
<223> OTHER INFORMATION: Chemically synthesized primer

<400> SEQUENCE: 2
cagtcaccca cttctgcttc                                          20

<210> SEQ ID NO 3
<211> LENGTH: 20
<212> TYPE: DNA
<213> ORGANISM: Artificial Sequence
<220> FEATURE:
<221> NAME/KEY: Pdx1 (F)
<223> OTHER INFORMATION: Chemically synthesized primer

<400> SEQUENCE: 3
ccaccccagt ttacaagctc                                          20

<210> SEQ ID NO 4
<211> LENGTH: 20
<212> TYPE: DNA
<213> ORGANISM: Artificial Sequence
<220> FEATURE:
<221> NAME/KEY: Pdx1 (R)
<223> OTHER INFORMATION: Chemically synthesized primer

<400> SEQUENCE: 4
tgtaggcagt acgggtcctc                                          20

<210> SEQ ID NO 5
<211> LENGTH: 20
<212> TYPE: DNA
<213> ORGANISM: Artificial Sequence
<220> FEATURE:
<221> NAME/KEY: NeuroD (F)
<223> OTHER INFORMATION: Chemically synthesized primer

<400> SEQUENCE: 5
gtcccagccc actaccaatt                                          20

<210> SEQ ID NO 6
<211> LENGTH: 20
<212> TYPE: DNA
<213> ORGANISM: Artificial Sequence
<220> FEATURE:
<221> NAME/KEY: NeuroD (R)
<223> OTHER INFORMATION: Chemically synthesized primer

<400> SEQUENCE: 6
cggcaccgga agagaagatt                                          20

```
<210> SEQ ID NO 7
<211> LENGTH: 20
<212> TYPE: DNA
<213> ORGANISM: Artificial Sequence
<220> FEATURE:
<221> NAME/KEY: Ptf1a (F)
<223> OTHER INFORMATION: Chemically synthesized primer

<400> SEQUENCE: 7
aaccaggccc agaaggttat                                          20

<210> SEQ ID NO 8
<211> LENGTH: 20
<212> TYPE: DNA
<213> ORGANISM: Artificial Sequence
<220> FEATURE:
<221> NAME/KEY: Ptf1a (R)
<223> OTHER INFORMATION: Chemically synthesized primer

<400> SEQUENCE: 8
cctctggggt ccacacttta                                          20

<210> SEQ ID NO 9
<211> LENGTH: 21
<212> TYPE: DNA
<213> ORGANISM: Artificial Sequence
<220> FEATURE:
<221> NAME/KEY: Notch1 (F)
<223> OTHER INFORMATION: Chemically synthesized primer

<400> SEQUENCE: 9
ttacagccac catcacagcc a                                        21

<210> SEQ ID NO 10
<211> LENGTH: 20
<212> TYPE: DNA
<213> ORGANISM: Artificial Sequence
<220> FEATURE:
<221> NAME/KEY: Notch1 (R)
<223> OTHER INFORMATION: Chemically synthesized primer

<400> SEQUENCE: 10
atgccctcgg accaatcaga                                          20

<210> SEQ ID NO 11
<211> LENGTH: 22
<212> TYPE: DNA
<213> ORGANISM: Artificial Sequence
<220> FEATURE:
<221> NAME/KEY: Hes1 (F)
<223> OTHER INFORMATION: Chemically synthesized primer

<400> SEQUENCE: 11
tcaacacgac accgcacaaa cc                                       22

<210> SEQ ID NO 12
<211> LENGTH: 21
<212> TYPE: DNA
<213> ORGANISM: Artificial Sequence
<220> FEATURE:
<221> NAME/KEY: Hes1 (R)
<223> OTHER INFORMATION: Chemically synthesized primer

<400> SEQUENCE: 12
ggtacttccc caacacgctc g                                        21
```

<210> SEQ ID NO 13
<211> LENGTH: 23
<212> TYPE: DNA
<213> ORGANISM: Artificial Sequence
<220> FEATURE:
<221> NAME/KEY: HNF6 (F)
<223> OTHER INFORMATION: Chemically synthesized primer

<400> SEQUENCE: 13
gcaatggaag taattcaggg cag                                        23

<210> SEQ ID NO 14
<211> LENGTH: 23
<212> TYPE: DNA
<213> ORGANISM: Artificial Sequence
<220> FEATURE:
<221> NAME/KEY: HNF6 (R)
<223> OTHER INFORMATION: Chemically synthesized primer

<400> SEQUENCE: 14
catgaagaag ttgctgacag tgc                                        23

<210> SEQ ID NO 15
<211> LENGTH: 17
<212> TYPE: DNA
<213> ORGANISM: Artificial Sequence
<220> FEATURE:
<221> NAME/KEY: Nkx6.1 (F)
<223> OTHER INFORMATION: Chemically synthesized primer

<400> SEQUENCE: 15
ccggtcggac gcccatc                                               17

<210> SEQ ID NO 16
<211> LENGTH: 21
<212> TYPE: DNA
<213> ORGANISM: Artificial Sequence
<220> FEATURE:
<221> NAME/KEY: Nkx6.1 (R)
<223> OTHER INFORMATION: Chemically synthesized primer

<400> SEQUENCE: 16
gaggctgcca ccgctcgatt t                                          21

<210> SEQ ID NO 17
<211> LENGTH: 20
<212> TYPE: DNA
<213> ORGANISM: Artificial Sequence
<220> FEATURE:
<221> NAME/KEY: Ins1 (F)
<223> OTHER INFORMATION: Chemically synthesized primer

<400> SEQUENCE: 17
gctggtagag ggagcagatg                                            20

<210> SEQ ID NO 18
<211> LENGTH: 20
<212> TYPE: DNA
<213> ORGANISM: Artificial Sequence
<220> FEATURE:
<221> NAME/KEY: Ins1 (R)
<223> OTHER INFORMATION: Chemically synthesized primer

<400> SEQUENCE: 18
cagagaccat cagcaagcag                                            20

```
<210> SEQ ID NO 19
<211> LENGTH: 19
<212> TYPE: DNA
<213> ORGANISM: Artificial Sequence
<220> FEATURE:
<221> NAME/KEY: Ins2 (F)
<223> OTHER INFORMATION: Chemically synthesized primer

<400> SEQUENCE: 19
ccctgctggc cctgctctt                                                  19

<210> SEQ ID NO 20
<211> LENGTH: 20
<212> TYPE: DNA
<213> ORGANISM: Artificial Sequence
<220> FEATURE:
<221> NAME/KEY: Ins2 (R)
<223> OTHER INFORMATION: Chemically synthesized primer

<400> SEQUENCE: 20
aggtctgaag gtcacctgct                                                 20

<210> SEQ ID NO 21
<211> LENGTH: 20
<212> TYPE: DNA
<213> ORGANISM: Artificial Sequence
<220> FEATURE:
<221> NAME/KEY: GAPDH (F)
<223> OTHER INFORMATION: Chemically synthesized primer

<400> SEQUENCE: 21
aactttggca ttgtggaagg                                                 20

<210> SEQ ID NO 22
<211> LENGTH: 20
<212> TYPE: DNA
<213> ORGANISM: Artificial Sequence
<220> FEATURE:
<221> NAME/KEY: GAPDH (R)
<223> OTHER INFORMATION: Chemically synthesized primer

<400> SEQUENCE: 22
acacattggg ggtaggaaca                                                 20
```

METHOD OF CULTURING PANCREATIC ISLET-LIKE TISSUES BY A TISSUE COMPLEX OF PANCREAS-DERIVED NON-ENDOCRINAL EPITHELIAL CELLS AND VASCULAR ENDOTHELIAL CELLS

TECHNICAL FIELD

The invention relates to culturing methods for producing insulin-producing tissues (IPTs), particularly by culturing pancreas-derived non-endocrinal epithelial cells (NEECs) and/or vascular endothelial cells (VECs) both isolated from pancreas, or by usage of the VECs to enhance the proliferation of native islet cells. The invention also relates to methods for enriching cells, which can be differentiated into insulin-producing cells, including a method of culturing the NEECs in the presence of left-over cells (LOCs) which are isolated from the primary culture of pancreatic cells containing the NEECs.

BACKGROUND

Islet transplantation has been recognized as an effective treatment for type-1 diabetes, but this procedure currently offers insulin independence to only less than 20% of the recipients and requires islets from more than one donor. Even for the recipients who have been transplanted islets from multiple donors, recent studies have indicated that only a small portion of the islets successfully engrafts; not to mention, donor tissue availability is always in shortage.

One strategy to offset the shortage of transplantable islets is an ex vivo culturing method to generate sufficient amounts of functional endocrine tissues from the islet progenitors possibly residing in the donor pancreas. Although a number of methods have been proposed, the ex vivo-generated islet-like tissues tend to produce meager amounts of insulin compared to those produced by native islets, often below 1% of the latter, and/or lack appropriate levels of glucose responsiveness, that is, unable to secrete more insulin in response to increasing concentrations of glucose.

Several studies have indicated the existence of islet progenitors in postnatal pancreas and in vivo regeneration of endocrinal cells by applying external stresses; for examples, administering toxins such as alloxan or streptozotocin, subjecting pancreas to such surgical treatments as pancreatectomy or tying a pancreatic duct called duct ligation. Recently, the duct ligation was found to render a massive pancreatic inflammation and cell apoptosis followed by a rapid proliferation of an islet progenitor cell population (Xu et al., 2008, Cell 132:197-207). Although the exact tissue localization of the progenitors in the pancreatic tissues has not yet been elucidated, a number of studies have found evidence that they reside in the ductal or centroacinar regions of the pancreas, as well as within islets indicated by a few other studies.

Despite the lack of exact identity of the progenitors, various methods to isolate them have been tested. One such method is cytometric sorting using a certain set of cell surface markers. A drawback of this method is that the amount of collected cells is often insufficient for expansion culture partly due to the damages caused by the sorting processes and possible biases from the cell surface markers. Another method is the selective expansion of target cells by culturing whole pancreatic discards. The pancreatic discards are seeded in culture containers with appropriate media and growth factors to promote the proliferation of prospective progenitors but not other non-target cells. One challenge in employing this method is to predict which and in what stage of cells need to be selectively expanded with a given culture protocol.

Another strategy to offset the shortage of transplantable islets is an ex vivo expansion of native islet cells. Islet cells such as beta cells are considered terminally differentiated thus difficult to promote their proliferation in vitro, which therefore requires an efficient method to do so.

SUMMARY OF THE INVENTION

The method of producing insulin-producing tissues (IPTs) by culturing, according to first aspect of the invention comprises: generating in vitro a tissue complex consisting of non-endocrinal epithelial cells (NEECs) and vascular endothelial cells (VECs) both of which are isolated or originate from the postnatal pancreas.

The method of producing insulin-producing tissues (IPTs) according to second aspect of the invention comprises: preparing vascular endothelial cells (VECs) and native islet cells, which have been isolated or originated from a postnatal pancreas; culturing in vitro the vascular endothelial cells (VECs) in a manner to form a monolayer; and seeding and growing the native islet cells on said monolayer.

The method of producing insulin-producing tissues (IPTs) according to third aspect of the invention comprises: preparing non-endocrinal epithelial cells (NEECs), which have been isolated or originated from a postnatal pancreas; culturing in vitro the non-endocrinal epithelial cells (NEECs) in a state adhered on a surface of a culture container or on a culture substrate ("culture substrate" is hereinafter used to include any form of scaffold); removing the non-endocrinal epithelial cells (NEECs) by treating with a tissue-dissociation enzyme from the culture container or culture substrate to leave left-over cells (LOCs) still adhering on the culture container or culture substrate: culturing the removed non-endocrinal epithelial cells (NEECs) and the left-over cells (LOCs) separately from each other; and culturing the non-endocrinal epithelial cells (NEECs) in a medium conditioned by, or in the presence of, the separately cultured left-over cells (LOCs) to form cell clusters.

BRIEF DESCRIPTION OF DRAWING

FIGS. 1A-1D are microscopic images showing a transition on course of NEEC growth; FIG. 1A show cells remained adhering on the collagen I-coated dish surface in the cell-capturing step (EXAMPLE 2);

FIG. 1B shows cell colonies that were induced to grow in a serum-free medium containing 20 ng/ml FGF-2 and 1400 U/ml LIF (EXAMPLE 3);

FIG. 1C shows cell colonies that further grew in a serum-free medium containing 10 mM nicotinamide, 0.02 micromolar ($10^{-6}$M) 2-mercaptoethanol and 10 ng/ml KGF for two days (EXAMPLE 4);

FIG. 1D shows formation of a dense monolayer of mostly epithelial cells after 7 days of culture in the same serum-free medium (EXAMPLE 4);

FIGS. 2A-2C are graphs showing cell densities in various colonies of the NEECs; FIG. 2A shows the differences in colony densities of NEECs cultured with the serum-containing medium for 18 and 36 hours after Accutase-treated pancreatic debris was seeded on collagen I-coated and antibody-treated plates;

FIG. 2B shows NEECs emerging from ductal tissues or whole pancreatic debris (all tissues) after stimulated with FGF-2 when the medium was changed to a serum-free medium);

FIG. 2C shows Brdu (bromodeoxyuridine)+NEECs passaged onto anti-Notch1 antibody-treated collagen I-coated culture containers (Anti-Notch1) and those onto untreated collagen I-coated culture containers (Untreated);

FIG. 3-1A shows the microscopic image of NEECs on the coated surface of the culture container after NEECs were cultured on collagen I-coated culture containers in the serum-free medium supplemented with 10 ng/ml EGF, 10 ng/ml HGF, 20 ng/ml BMP7 and 4 micromolar rock inhibitor, on which transwell inserts containing left-over cells (LOCs) were loaded (Arrows indicate NEEC clusters that grew in size and roughly align in positions in culture with LOC clusters in the transwell insert shown in FIG. 3-1B); FIG. 3-1B shows the LOCs in the transwell insert after being co-cultured with NEECs on the coated surface of the culture container (Arrows indicate LOC clusters); FIG. 3-1C shows NEEC clusters one week later having more mature three dimensional structures;

FIG. 3-2 is a graph showing the difference in the number of clusters that formed with or without LOCs in inserts;

FIG. 3-3 shows mRNA expression of Pdx-1 and Ins1 for LOCs, NEECs cultured with or without LOCs in inserts and native islets;

FIG. 4A shows the fluorescent microscopic images of NEECs stained with an anti-insulin primary and Cy3-conjugated secondary antibodies and DAPI (4',6-diamino-2-phenylindole) for cells grown in the presence of Atorvastatin (to be referred to as "ATS-treated" and images are shown in right-hand part) or absence of the Atorvastatin (as "Control", shown in left-hand part), where the upper image panels show insulin-immuno-stained cells, and the lower panels DAPI-stained corresponding nuclei. The size bar in an upper-left panel represents 100 micrometer for all panels;

FIG. 4B shows percentage of insulin-positive cells obtained from these images;

FIG. 5A is a set of fluorescent microscope images showing the expression of Ngn3 in the nuclei of NEECs that were either treated with all-trans retinoic acid (RA) and cyclopamin KAAD (Cycl-K) for 24 hours (left-hand images designated as "Cycl-K+RA") or left untreated (right-hand images designated as "Control"), where images of upper panels were obtained by that nuclei of the cells were counter-stained with DAPI to confirm the nuclear localization of Ngn3, and the size bar in lower right-hand panel indicates 5 micrometer for all panels;

FIG. 5B is a graph showing percentages of Ngn3-positive cells in the NEECs;

FIGS. 6A-6B show the relative expressions of genes: Ngn3, Pdx1, Neuro D, Ptf1a (in FIG. 6A), and Notch1, Hes1, HNF6 and Nkx6.1 (in FIG. 6B) based on semi-quantitative RT-PCR (Reverse Transcription Polymerase Chain Reaction) of the NEECs ("1", pancreatic discards; "2", NEECs after 5 days of culture in serum-free media; "3", NEECs subsequently cultured with media containing all-trans retinoic acid and cyclopamine KAAD for 24 hours; and "4", NEECs culture control of "3");

FIG. 6B shows the relative expressions of genes: Notch1, Hes1, HNF6 and Nkx6.1 as indicated above;

FIG. 7-2 shows a graph indicating numbers of IPTs (100-200 micrometer diameter) generated either from NEECs alone or a tissue complex of NEECs and VECs;

FIG. 8-1 shows the images of IPTs generated from NEECs and matured for 20 days—IPTs generated from NEECs alone (A) and IPTs generated from a tissue complex of 80% NEECs and 20% VECs (B) (Size bars represent 30 micrometer);

FIG. 8-2 is a graph showing percentage of the insulin-producing cells in the IPTs;

FIGS. 9A-9C show the image and graphs for insulin mRNA expressions amplified by semi-quantitative PCR (in FIG. 9A, M represents DNA size markers);

FIG. 9B is the graph for insulin 1 expression;

FIG. 9B is the graph for insulin 2 expression;

FIGS. 10A-10B show secretion of C-peptide (FIG. 10A) and insulin (FIG. 10B) upon stimulation of IPTs with low (5 mM) and high (20 mM) glucose concentrations in KREBS buffer medium;

FIG. 11-1 shows an image of islet cells grown on a monolayer of VECs on a chamber slide;

FIGS. 11-2 shows a series of immunocytochemical images of islet cells seeded on a monolayer of VECs on a chamber slide (A, B and C) and those seeded on a coated surfaces of a chamber slide (D, E and F);

FIG. 11-3 shows a graph showing percentages of bromodeoxyuridine-positive cells (% Brdu+ cells) of islet cells grown on VECs and on Matrigel;

FIG. 12A shows the changes in blood glucose levels measured for a diabetic mouse into which 700 IEQ's of IPTs generated from the pancreatic tissues of donor mice of the same strain were transplanted under the kidney capsule; and FIG. 12B shows insulin+ cells under the kidney capsule removed after the measurement of blood glucose levels for the indicated period.

DETAILED DESCRIPTION OF THE INVENTION

Figures 1, 3:
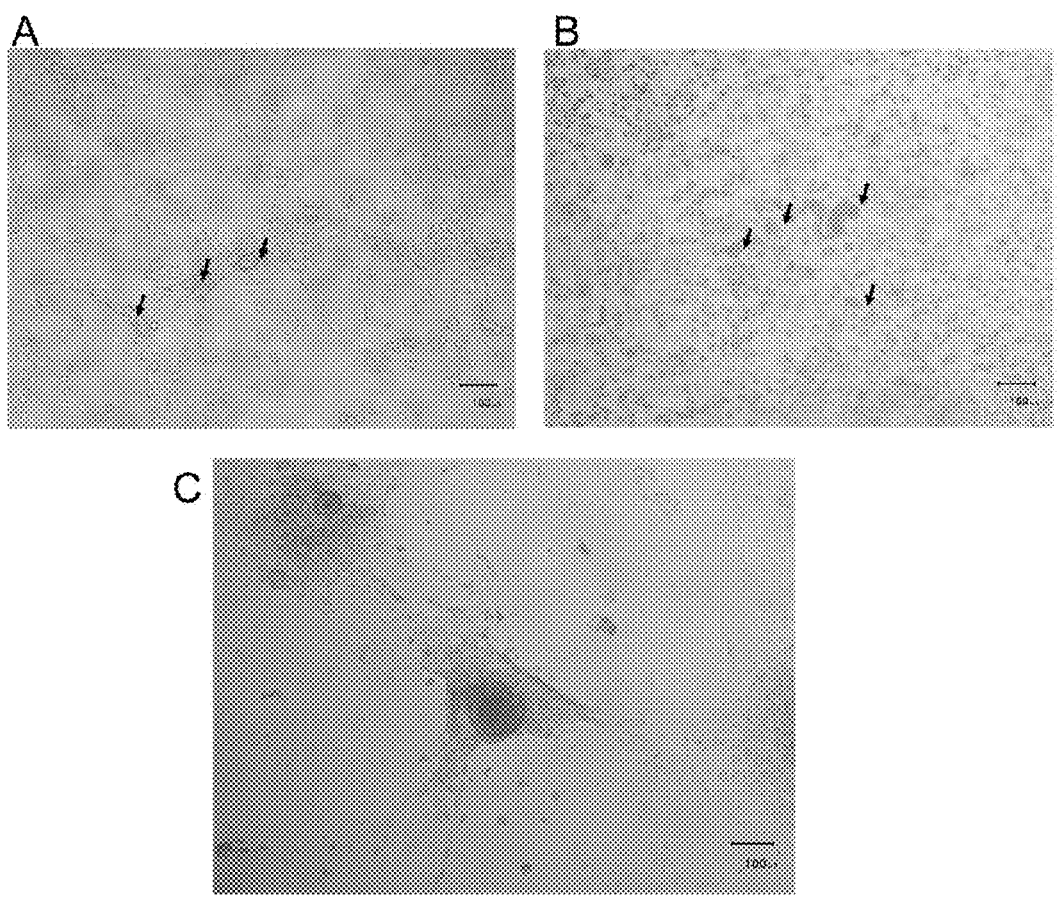

The invention provides the culturing methods for the enhancement of the formation and endocrinal functions of insulin-producing tissues (IPTs), particularly a method of culturing pancreas-derived non-endocrinal epithelial cells (NEECs) with vascular endothelial cells (VECs) both isolated from pancreas to enhance the formation of IPTs. It is also aimed to provide another usage of the VECs to enhance the proliferation of native islet cells. Thus, it is to provide the use of specific cell isolation and culture methods to allow for the expansion of NEEC colonies to generate IPTs endowed with pancreatic-islet-like characteristics and for the enhanced proliferation of native islets for the treatment of type-1 and type-2 diabetes.

In a first preferred embodiment, said NEECs are cultured from discarded tissues after the isolation of islets, and their population is initiated by a method comprising following (1) and (3), and preferably further comprising following (2).

(1) cell-capturing by seeding said pancreatic discards in a serum-containing culture medium, on a culture container or culture substrate that is coated with cell adhesion material such as collagen, and preferably with antibody such as that against c-Met (HGF receptor) and/or E-cadherin, and then by subsequently allowing the culture to stand; for example, for 8 to 56 hours at around 37° C. and enhanced $CO_2$. In an example, the cell-capturing is made in RPMI1640 with 10% (v/v) FCS (fetal calf serum) in culture containers coated with 0.2 mg/ml rat tail collagen I and further coated with anti-E- cadherin antibody and/or anti-c-Met (HGF receptor) antibody with concentration ranging between 1:100 and 1:1000; and the tissues are cultured at around 37° C. and 5% $CO_2$ for 24 to 36 hours.

(2) colony induction by replacing the serum-containing medium in the cell-capturing (1) with a first serum-free medium containing FGF-2 or other fibroblast growth factors or containing the fibroblast growth factor as well as insulin-transferrin-sodium selenite supplement or other growth factor supplements, and preferably further containing LIF (Leukemia Inhibitory Factor); and by continuing of culturing in the serum-free medium; for at least 8 hours at around 37° C. and enhanced $CO_2$ for example. Preferably, the first serum-free medium contains the fibroblast growth factor in a range of 2-40 ng/ml more preferably in a range of 5-30 ng/ml and/or LIF in a range of 100-15000 U/ml more preferably in a range of 300-5000 U/ml. In an example, the first serum-free medium contains 1 g/l ITS (Insulin-Transferrin-Selenium supplement; for example, 5 microgram/ml insulin, 5 microgram/ml transferrin, 5 ng/ml sodium selenite), 0.2% BSA (bovine serum albumin), 20 ng/ml recombinant human FGF-2 and 1400 U/ml recombinant human LIF (Leukemia Inhibitory Factor) in DMEM/Ham's F-12 containing 10 mM D-glucose and cultured for at least 24 hours. This step can be skipped, and a cell-capturing step (1) may be directly followed by an initial colony-growing step (3) indicated below.

(3) an initial colony-growing by changing the first serum-free medium in the colony induction (2) to second serum-free medium containing human KGF (keratinocyte growth factor), or containing the human KGF as well as insulin-transferrin-sodium selenite supplement or other growth factor supplements, and by culturing until clonal colonies of the NEECs with the cell size ranging 10-30 micrometer in diameter emerge. Preferably, the second serum-free medium contains KGF in a range of 1-100 ng/ml, more preferably in a range of 3-30 ng/ml. The second serum-free medium preferably contains the growth factor supplement in a range of 0.1-10 g/L. For example, the second serum-free medium contains 1 g/L ITS (5 microgram/ml insulin, 5 microgram/ml transferrin, 5 ng/ml sodium selenite), 0.2% BSA, 10 mM nicotinamide, and 10 ng/ml recombinant human KGF (keratinocyte growth factor) in DMEM/Ham's F-12 containing 7 mM D-glucose; and culturing is made for at least 2 to 7 days, at around 37° C. and enhanced $CO_2$ for example. To mitigate the growth of fibroblast-like cells 0.02 micromolar 2-mercaptoethanol may be added to the medium if necessary. To prevent the infestation of mycoplasma, mycoplasma-removing agents may be added to the medium. The media are preferably replenished in every 2-3 days until a substantial number of clonal colonies of NEECs with the size ranging 10-30 micrometer in diameter emerge.

In the second preferred embodiment, said NEECs are passaged for their selective expansion by the techniques with the following (4) through (6):

(4) the first cell-removal, that is, removing the NEECs in the initial colony-growing (3) of the first preferred embodiment from the culture containers by treating them with a tissue-dissociation enzyme solution; and by filtering and/or centrifuging to remove the NEECs from the second serum-free medium. For example, Accutase is used for the removing; and the removed cells are filtered through a 40 micrometer mesh and centrifuged at or below 160×g for less than 4 min.

(5) the second cell-removal or cell detaching, that is, removing the left-over cells (LOCs) that are epithelial cells tightly attaching together from the culture containers in the first cell-removal step (4) by adding stronger cell-dissociation or partially protein-degenerating agent such as trypsin-EDTA (ethylene diamine tetraacetic acid) for example, and by subjecting the LOCs for 1-15 min at around 37° C. for example. In a detailed example, the LOCs are removed with 0.05% trypsin-EDTA at 37° C. for 3 to 5 min; and these cells after washed with a serum-free medium are transferred into transwell inserts and cultured in a bath of the medium for later use.

(6) NEECs obtained in the first cell removal are cultured in a condition medium having been conditioned by the left-over cells (LOCs) that had been obtained in the second cell removal. In preferred examples, the removed cells obtained in the first cell removal (4) are seeded on new culture containers as in the cell-capturing step (1) of the first preferred embodiment or other culture containers; and the culture containers are loaded with the transwell inserts (for example, Millipore Co.) containing LOCs obtained by the second cell removal. Through porous bottom of the transwell inserts, a culture medium inside the transwell inserts is common or communicated with a medium for the NEEC culture on the bottom of the culture container. Preferably, the NEECs obtained in the first cell removal (4) are seeded on the culture container or the culture substrate that is coated with collagen containing the KGF or containing the KGF and anti-Notch 1 antibody; and the NEECs are cultured in a third serum-free medium supplemented with atorvastatin. Here, the KGF or KGF and anti-Notch 1 antibody may be replaced with rock (Rho-associated coiled-coil containing protein kinase) inhibitor or with the mixture of rock inhibitor, EGF (epidermal growth factor) and HGF (hepatocyte growth factor) as well as BMP-4 or BMP-7.

For example, the collagen solution for coating the containers is prepared with 10 ng/ml KGF, and the coated surface is further treated with anti-Notch 1 antibody with the final concentration of 1:100 to 1:1000. Alternatively, the collagen coating is not prepared with KGF nor further treated with anti-Notch 1 antibody; instead, KGF in the culture medium of the first cell-removal step (1) is replaced with: HGF (hepatocyte growth factor) more than 10, or 20 ng/ml and less than 30 or 20 ng/ml (20 ng/ml for example); EGF (epidermal growth factor) more than 10, 15, 20 or 30 ng/m and less than 50 or 40 ng/m (40 ng/ml for example); and rock (Rho-associated coiled-coil containing protein kinase) inhibitor more than 2, 4, 8 or 14 micromolar and less than 25, 20, 14 or 8 micromolar (4 micromolar for example). After the removed NEECs obtained in the cell-removal (4) are seeded on the containers and optionally loaded with transwell inserts containing LOCs, the culture medium may preferably be further supplemented with 0.01-1.0 micromolar, more preferably 0.03-0.3 micromolar, and for example, 0.1 micromolar atorvastatin and may preferably be further supplemented with more than 10 or 15 ng/m and less than 40 or 30 ng/m of BMP7 (20 ng/ml BMP7 for example) to enrich NEECs in the propensity toward becoming endocrinal cells upon differentiation later. The media are replenished with 40% conditioned medium in every 2-3 days until a substantial number of clonal colonies of NEECs are grown. The clonal colonies of NEECs spontaneously form cell clusters that can be passaged for a further enrichment to increase their propensity toward forming the tissue complex upon differentiation.

In the third preferred embodiment, said NEECs upon expansion or passaging contain cells that express Hes1, a downstream target of Notch signaling, and later identified as Ngn3-positive cells upon treatment with all-trans retinoic acid and cyclopamine KAAD ((3-Keto-N-(aminoethyl-aminocaproyl-dihydrocinnamoyl)cyclopamine), thereby, signifying the identity of progenitors competent for generating insulin-producing cells.

In the fourth preferred embodiment, said VECs are cultured from discarded tissues after the removal of islets, that their population is initiated by the cultural techniques with the following (7) and (8):

(7) seeding said discarded tissues themselves or floating tissue debris removed in the cell-capturing step (1) of the first preferred embodiment in a second serum-containing culture medium, on a culture container or culture substrate that is coated with collagen or other cell adhesion material; and culturing in the second serum-containing culture medium. Preferably, this culturing includes expansion of the VECs subsequent to said seeding; replenishing of the culture medium; and purification of the VECs by using an antibody and magnetic beads. Replenishing of media is performed in such a way that non-adherent cells and tissues after said expansion are removed and briefly washed with physiological solutions such as phosphate buffer solution (PBS) for example, before replenished with a fresh serum-containing culture medium. More preferably, the fresh serum-containing culture medium contains anti-fungal agents such as fungizone (trade name, Invitrogen Co.).

The second serum-containing culture medium is, for example, RPMI1640 containing 70-100 microgram/ml EGGS (endothelial cell growth supplement) and 20% (v/v) FCS, which has been heat-inactivated at 65.5° C. for 60 to 70 min., in culture containers coated with 1.8 mg/ml rat tail collagen I. For example, the non-adherent tissues after 18 hours of culture are removed, and adhering cells and tissues are briefly washed with PBS before replenished with a fresh medium containing 0.1% (v/v) fungizone.

(8) purification of VECs by antibody and magnetic microbeads, preferably by using antibody-conjugated substrates such as antibody-conjugated microbeads, such as that having an anti-CD31 antibody. Preferably, the said seeding and said replenishing described in (7) are repeated to further expand the purified VECs.

In the fifth preferred embodiment, said VECs are seeded on culture containers to produce a near-confluent monolayer in the medium specified in the fourth preferred embodiment, then cells or cell clusters dissociated from isolated and purified native islets are seeded on the VEC monolayer to enhance the cells or cell clusters of the islets to proliferate. Preferably, the VECs are subjected to the seeding and culturing (7) and/or the purification (8) in the fourth preferred embodiment, before forming the VEC monolayer.

In an embodiment according to the first, fourth or fifth preferred embodiment, said VECs are either derived from the same donor tissues from which said NEECs are isolated or tissues of the recipient to which said IPTs or native islets are to be transplanted.

In an embodiment according to anyone of the preceding embodiments, said IPTs are generated by allowing the formation of a tissue complex of said NEECs and VECs using the cultural techniques with the following (9)-(11):

(9) removing said NEECs and VECs as in the first cell-removal (4) of the second preferred embodiment and of generating a tissue complex of NEECs and VECs in a low adherence culture container.

(10) generating said tissue complex by placing the said NEECs and VECs obtained in said removing (9) into a low adherence culture container having a serum-containing differentiation culture medium and swirling of the low adherence culture container until initial formation of the tissue complex is made.

The two kinds of cells preferably have mixing ratios of cell numbers in a range of 97/3 to 70/30, more preferably in a range of 97/3 to 75/25 or 95/5 to 70/30, further preferably in a range of 90/10 to 70/30 or 95/5 to 75/25, and still more preferably in a range of 90/10 to 75/25.

Preferably, the culture serum-containing differentiation culture medium includes Activin, other growth factors, and $CaCl_2$. More preferably, the culture serum-containing differentiation culture medium further includes bone morphogenetic protein such as BMP-7 or BMP-4. Still more preferably, the culture serum-containing differentiation culture medium includes Betacellulin and/or Exendin-4. In preferred examples, included are Activin, Betacellulin, HGF (Hepatocyte growth factor), Gastrin, IGF (Insulin-like growth factor)-1, KGF, VEGF (Vascular Endothelial Growth Factor), BMP7, Exendin-4, ascorbic acid and $CaCl_2$. In a detailed example, the culture medium contains DMEM/Ham's F-12 with 20 mM D-glucose supplemented with 2% (v/v) FCS, 2 ng/ml Activin A, 5 ng/ml Betacellulin, 20 ng/ml HGF, 20 ng/ml Gastrin, 20 ng/ml BMP7, 20 ng/ml IGF-1, 5 ng/ml KGF, 20 ng/ml VEGF, 20 ng/ml Exendin-4, 10 mM nicotinamide, 0.1 mM ascorbic acid and 1 mM $CaCl_2$. The swirling motion of the container is preferably made until spherical clusters of IPTs appear in the medium, preferably at a speed of less than 10, 15, or 20 rpm; for example, at 37° C. and 5% $CO_2$ for 18 to 24 hours.

(11) maturing said IPTs with the same procedures as in said generating (10) except that the culture container is horizontally placed without motion and culture medium has no $CaCl_2$. In preferred examples, the culture medium is to be replenished every 1-2 days for the entire maturation period of about 20 days.

In an embodiment according to anyone of the preceding embodiments antibiotics to be added to the culture media are 50-100 U/ml penicillin and 50-100 microgram/ml streptomycin, or streptomycin may be replaced with 50-100 U/ml gentamycin.

In an embodiment according to anyone of the preceding embodiments, the stock solution of ITS (insulin-transferrin-sodium selenite supplement) to be added to the culture media includes about 5 microgram/ml insulin and about 5 microgram/ml transferrin and includes sodium selenite preferably in a range of 0.5 to 5 ng/ml, more preferably in a range of 0.75 to 2.5 ng/ml, and around 1.25 ng/ml for example.

In an embodiment according to any one of the preceding embodiments, said IPTs comprise greater amounts tissues with larger proportions of insulin-producing cells than those without the method indicated in the embodiments.

In an embodiment according to any one of the preceding embodiments, said IPTs comprise cells that produce more insulin than tissues formed by those without the technique indicated in the embodiments.

In an embodiment according to any one of the preceding embodiments, said functions of IPTs comprise the secretion of less than 5%, 10%, 40%, 60%, 80% or 100% of insulin produced by con-specific native islets.

In an embodiment according to any one of the preceding embodiments, said functions of IPTs comprise greater glucose-responsiveness in insulin secretion than that without the technique indicated in the embodiments.

In an embodiment according to any one of the preceding embodiments, said functions of IPTs comprise the normalization of glucose-controlling ability of a diabetic recipient upon the transplantation of the IPTs into the recipient.

In an embodiment according to any one of the preceding embodiments, said proliferation of native islets is increased in greater degrees than those without the method indicated in the embodiments.

Here we describe further detailed embodiments of an in vitro culture method that enables the generation of non-endocrinal epithelial cells (NEECs) obtained from postnatal pancreas into insulin-producing tissues (IPTs) which contain endocrinal cells that secrete insulin up to 10% of that produced by native islets with appropriate degrees of glucose responsiveness.

We employ a culturing method using at least two among following three different groups of cells in the first and third aspect of the invention. One is NEECs isolated from pancreas. These cells can be defined as progenitor cells of epithelial characteristics residing within or near pancreatic ducts or as centroacinar cells. Recently, these cells were labeled with Aldefluor dye, which utilizes the high enzymatic activity of aldehyde dehydrogenease in progenitor cells (Rovira et al., 2010, PNAS 107:75-80), and are predicted to be more abundant than previously thought.

Pancreatic discards after the removal of islets, such as collagenase-digested pancreatic discards, are seeded with a serum-containing culture medium, such as RPMI1640 medium with 10% FCS, on culture containers or culture substrates coated with collagen I or the like. This initial incubation allows adherent cells and tissues to adhere to the coated surface, thereby, capturing of the cells, predominantly of the NEECs. For such capturing, the culture is allowed to stand, preferably for 8 to 56 hours, more preferably for 12 to 48 hours; preferably at around 37° C. with enhanced concentration of $CO_2$. On course of such capturing, initial incubation or culturing of the NEECs takes place. Then the serum-containing culture medium is replaced by a first serum-free medium containing FGF-2, or analogous growth factor, to stimulate proliferation preferably for 8 to 48 hours, more preferably for 12-36 hours; for example, for 24 hours. After this period the medium is further replaced with another or second serum-free culture medium, preferably containing KGF or analogous growth factor and/or some growth inhibitor for the fibroblast-like cells; such as a serum-free medium containing 0.1 nM 2-mercaptoethanol, 0.2% BSA, 1 g/L ITS, 10 mM nicotinamide and 10 ng/ml KGF; preferably at around 37° C. with enhanced concentration of $CO_2$. 2-mercaptoethanol inhibits growth of fibroblast-like cells, which tend to disrupt the growth of epithelial cells. An ITS stock solution to be added to the serum-free medium preferably contains 5 microgram/ml insulin, 5 microgram/ml transferrin, and 0.5, 1.25, 2.5, 5, or more preferably 1.25 ng/ml sodium selenite.

Clonal colonies of NEECs grow in size typically for 7 to 10 days of culture. Thus, the culturing in the second serum-free medium is replenished preferably in 2-3 days, preferably for 3-20 days, more preferably for 5-15 days; preferably at around 37° C. with enhanced concentration of $CO_2$. By such initial colony growth, clonal colonies of the NEECs with the size ranging 10-30 micrometer in diameter emerge. In any of the serum-containing or serum-free media used in the cultures described above, mycoplasma-removing agents can be added to discourage mycoplasma infestation if necessary.

The serum-free medium is subsequently replenished preferably in every 2 to 3 days with the same medium but with decreased sugar concentrations, such as 7 mM D-glucose or below, to prevent spontaneous generation of insulin-producing cells.

In preferred embodiments, adopted is a multi-level stimulation of Notch receptor which functions as a key signal transducer to switch on the cell cycles. When sufficient numbers of monolayer cells are grown greater than 70% confluence, the cells are dissociated from the culture containers with Accutase, filtered through a 40 micrometer nylon mesh, and seeded on culture containers coated with KGF-embedded collagen I and further treated with anti-Notch I antibody.

The passaging method of the present invention utilizes the two-way Notch-activating stimulation: one through the extracellular stimulation of Notch receptor by means of the anti-Notch 1 antibody described above, or other analogous Notch-activating antibody; and the other through the intracellular stimulation by atorvastatin or possibly other analogous statins that have Notch pathway-activating property. Statins are HMG-CoA reductase inhibitors, and these include atorvastatin and simvastatin among others. Atorvastatin is known to promote the expression of Presenilin 1, a positive inducer of potential endocrinal progenitor cells. Concentration of the atorvastatin, simvastatin or other statins in the modified serum-free medium is preferably 0.01-1.0 micromolar, more preferably 0.03-0.3 micromolar, and 0.1 micromolar for example.

Alternatively, the collagen coating is not prepared with KGF nor further treated with anti-Notch 1 antibody; instead, KGF in the culture medium of the initial colony-growing step (3) is replaced with 10, 15, 20 and 30, and more preferably, 20 ng/ml HGF, 10, 15, 20, 30, 40 or 50, and more preferably, 40 ng/ml EGF and 2, 4, 6, 8 or 10, and more preferably 4 micromolar rock inhibitor. The culture medium is further supplemented with atorvastatin and 10, 15, 20 or 30, and more preferably 20 ng/ml BMP4 or BMP7 to enrich NEECs in the propensity toward becoming endocrinal cells upon differentiation later.

Another group of cells to be used in the culture are epithelial cells tightly attaching together forming cell clumps. These cells proliferate rapidly under the herein-described culture conditions and are possibly progenitors of acinar cells and/or those de-differentiated to have duct-like or duct-progenitor-like phenotypes. The initial serum-free medium culture contains substantial amount of these epithelial cell clumps, which enhance the proliferation of the NEECs supposedly by secreting some unidentified paracrine factors. These cells are left adhering to the culture containers after the NEECs are removed by treating with tissue-dissociation enzyme such as Accutase treatments, thus called "left-over cells (LOCs)." These are then removed from the culture containers by stronger dissociation enzyme such as proteinase; for example, by treating with 0.05% trypsin-EDTA at 37° C. for 3 to 5 min, washed with the serum-free medium and are transferred into transwell inserts and placed in the medium for enhancing the proliferation of the NEECs.

The third group of cells are vascular endothelial cells (VECs) that can be cultured from the tissue debris collected from the culture for the capturing of the NEECs. The VECs are collected preferably after 6-54 hours, more preferably after 9-36 hours from the floating debris in the culture for capturing adherent cells or tissues described earlier. Cultured VECs are purified using anti-CD31 antibody-conjugated magnetic beads.

One embodiment of the invention provides a method of generating a tissue complex from NEECs and VECs in a low adherence culture container; the two kinds of cells preferably have mixing ratios of cell numbers in a range of 97/3 to 75/25, more preferably in a range of 95/5 to 70/30; that is, preferably with a mixing ratio ranging from 3% to 25% and more preferably with a ratio of 5% to 30% in respect of cell numbers of the NEECs to a sum of cell numbers of the NEECs and the VECs. The tissue complex is generated by swirling of the low adherence culture container preferably for 6 to 72 hours, more preferably for 9 to 48 hours, further preferably for 18 to 24 hours, preferably at around 37° C. with enhanced concentration of $CO_2$. Swirling is made until spherical clusters of IPTs appear in a culture medium. The culture medium used here preferably contains Activin, Betacellulin, HGF, Gastrin, IGF1, KGF, VEGF, BMP7, Exendin4, ascorbic acid and $CaCl_2$.

In preferred embodiments, adopted is maturing of said IPTs with the same methods mentioned earlier except for the culture container horizontally placed without motion and culture medium without $CaCl_2$. The culture medium is to be replenished every 1-2 days for the entire maturation period of about 20 days.

The present invention describes a new method to enhance the formation and function of insulin-producing tissues (IPTs) by generating in vitro a tissue complex of non-endocrinal epithelial cells (NEECs) and vascular endothelial cells (VECs) both obtained from postnatal pancreas. The tissue sources from which the VECs are isolated and the physiological state of the VECs themselves are both important in the present invention. Since phenotypic characters of vascular endothelial cells are heterogeneous partly depending on the kinds of the organs, tissues and cells where they reside (Crivellato et al., 2007, J. Anat. 211:415-427), the tissue or organ specificity of the VECs is likely to be a crucial factor in enhancing the differentiation of NEECs into IPTs and/or the proliferation of native islet cells. In addition, VECs to be used together with NEECs for the generation of a tissue complex and subsequently IPTs are preferably to be fenestrated as a phenotype is usually observed in vascular endothelial cells in native islets. Thus, the differentiation medium used in this invention contains VEGF, which is known to stimulate VECs to form fenestration.

The methods of enhancing the formation and function of IPTs are designed in two steps: one is the isolation and expansion of two types of cells, NEECs and VECs, and the other is the generation of a tissue complex from these two kinds of cells. These steps are described in detail herein the respective sections under the headings of EXAMPLE and/or claims.

To isolate cell populations that may contain islet progenitor cells, one can sort cells with various surface markers by cytometry. A disadvantage of this method is that the amount of sorted cells is often insufficient for culture expansion of progenitors which usually do not proliferate indefinitely and subject to the damages caused by the sorting processes. Another disadvantage is that a set of surface markers used may create a sorting bias due to the variations between individual cell samples; thus, whether the cells obtained are the target progenitors can be more rigorously evaluated only after the generation of functional endocrine cells.

To this end, we employ a cell culture approach that allows for the selective expansion of the target progenitor cells. The pancreatic discards, the left-over tissues after islets have been removed, are seeded in culture containers with appropriate media and growth factors to promote the proliferation of prospective progenitors but not non-target cells. In previous studies, attempts have been made to design a number of procedures to selectively expand progenitor cells that could generate insulin-producing cells. For example, Todorov et al. (2006, Pancreas 32:130-138) expanded pdx1-expressing epithelial cells using human pancreatic tissue discards with a serum-containing medium in collagen I-coated flasks. This procedure has set the foundation of our current invention, and various modifications have been made with respect to the choice of media and growth factors. We use RPMI1640 supplemented with 10% heat-inactivated FCS to promote the selective cell adherence on collagen I-coated surfaces as Bonner-Weir et al. (2000, PNAS 97:7999-8004) and Katdare et al. (2004, J. Endocrinology 182:105-112) used in their selective expansion methods. In these studies, the culture medium was switched to a serum-free medium containing insulin-trasferrin-selenium (ITS), 5-10 mM nicotinamide and 10 ng/ml KGF (FGF-7). Nicotinamide has been said to promote epithelial cell growth. Katdare et al. (2004) also used 2-mercaptoethanol to discourage the growth of fibroblast-like cells. We have modified their methods by adding another intermediate step for clonal colony induction, where FGF-2 and LIF are used as supplements in order to indiscriminately promote the growth of adherent cells for 24 hours. Then the culture medium is changed to another serum-free medium supplemented with 2-mercaptoethanol, nicotinamide and KGF, which allows for further cell proliferation. Within the following period of 2-7 days, a substantial number of clonal colonies of epithelial cells with the size ranging 10-30 micrometer in diameter emerge. These cells at least in the initial expansion stage do not form tightly-bound epithelial sheets but remained as clusters of loosely-bordered single cells. We have named these cells "non-endocrinal epithelial cells (NEECs)," indicating their heterogeneous groups of cells within a larger category of epithelial cells that include progenitors not yet having attained endocrinal functions. To prevent premature generation of endocrine cells, glucose concentrations in the serum-free media are kept at or below 7 mM throughout the rest of the NEEC cultures. In this initial culturing step, we allow the tightly-attaching epithelial cells to grow with NEECs because the former are likely to secrete certain unidentified growth factors that seem to promote the growth of the latter, NEECs. We have named these tightly-attaching epithelial cells "left-over cells (LOCs)," which are left adhering on culture containers from which NEECs were removed by Accutase treatment described earlier. LOCs are then removed by trypsinization later.

For the collagen-coated culture containers, well plates or culture dish, we modify its surface property to increase the adhesiveness of NEECs; this is done by treating the collagen-coated container with anti-E cadherin antibody and anti-cMet antibody in PBS with concentrations ranging between 1:100 and 1:1000 at RT (room temperature, or at around 25° C.) for one hour. This antibody treatment is to increase the chance of epithelial cells' adherence relative to that of other types of cells. Epithelial cells among other types of cells express E-cadherin, a cell-to-cell adhesion molecule, which is also expressed in pancreatic endocrine progenitors; thus, they are predicted to adhere to anti-E cadherin antibody-coated surfaces. HGF receptor, which is synonymous to c-Met, is one of the cell surface molecules that characterize progenitors some of which are competent to become islet endocrine cells (Suzuki et al., 2004, Diabetes 53:2143-2152). Indeed, the antibody treatment increased the yield of epithelial cells per coated surface (FIG. 2A); interestingly, a combination of both antibodies yielded somewhat lower cell yields than either one alone.

The progenitor populations isolated from adult pancreas are likely to stop proliferating upon passaging (Seaberg et al., 2004, Nature Biotechnology 22:1115-1124). Ta et al. (2006, Stem Cells 24:1738-1749) overcame this proliferation stasis by inducing epithelial-mesenchymal transition (EMT) with BMP-4. According to their work, post-EMT fibro-like cells rapidly proliferated. Once the cultures yielding an enough amount of cells, epithelial characteristics were restored by the reverse process, mesenchymal-epithelial transition (MET) before the generation of islet-like tissues. One drawback in this transitory culture method was that the resulting islet-like tissues secreted a meager amount of insulin, suggesting that it possibly hindered the functional outcome of resulting tissues. In contrast, islet-like tissues generated from epithelial cells such as those by Bonner-Weir et al. (2000) or Katdare et al. (2004) produced larger amounts of insulin. Although the latter two studies did not indicate detailed methods of passaging, we have simulated some of their basic culturing techniques to improve the uniformity of epithelial cells upon passaging without inducing EMT.

To improve the proliferation of NEECs after passaging, we employ two-way stimulation of Notch signaling, a key signal transducer to switch on the cell cycles. One way is through the extracellular stimulation of Notch receptor by using anti-Notch 1 antibody, and the other way is through the intracellular stimulation by using atorvastatin. When sufficient numbers of monolayer cells in the primary culture are grown greater than 50%, 60%, 70%, 80%, 90% or 100% confluence, and more preferably 70% confluence, the NEEC cells are removed as single cells or small cell clumps from the culture containers with Accutase. Exclusion of larger cell clumps especially LOCs is warranted by filtering the cell suspension through a filter fabric or other filter material such as a nylon mesh, with about 10, 20, 30, 40, 50, 70 or 100 micrometer, and more preferably, 40 micrometer mesh size. Filtered NEECs are seeded at about a ⅔, ¾ or ⅘, and more preferably ¾ of the original cell density on culture containers coated with KGF-embedded collagen I and further treated with an anti-Notch 1 antibody at a dilution factor of 1:1000 (Millipore Co.). Anti-Notch 1 antibodies of a particular group are known to induce Notch receptor activation in muscle cell regeneration (Conboy et al., 2003, Science 302:1575-1577).

The NEECs are then grown in a modified serum-free medium by adding 0.1 micromolar atorvastatin, which is known to positively select for potential endocrinal progenitor cells. Cras-Meneur et al. (2009, Genes & Development 23:2088-2101) using transgenic mice model demonstrated that presenilin 1 and 2 at the catalytic core of γ-secretase are essential for Notch signaling and acquisition of endocrine fate by Ngn3$^+$ progenitors. Presenilin 1 is known to be upregulated by atorvastatin in neural cell regeneration after stroke (Chen et al., 2008, Stroke 39:220-226). Therefore, we use atorvastatin to increase endocrinal progenitor cells within a pool of epithelial cells although other statins may produce similar effects. For NEEC cultures, the serum-free medium can be further modified by replacing KGF with: HGF in a range covering 10, 15, 20 and/or 30, and more preferably, 20 ng/ml HGF; EGF in a range covering 10, 15, 20, 30, 40 and/or 50, and more preferably, 40 ng/ml EGF; and/or rock inhibitor in a range covering 2, 4, 6, 8 and/or 10, and more preferably 4 micromolar rock inhibitor. For NEEC cultures, the serum-free medium can be further supplemented with: atorvastatin in a range of 0.01-1.0 micromolar, more preferably 0.03-0.3 micromolar, and 0.1 micromolar for example; and BMP in a range covering 10, 15, 20 and/or 30, and more preferably about 20 ng/ml BMP4 or BMP7 to enrich NEECs in the propensity toward becoming endocrinal cells upon differentiation later. Alter dissociated NEECs are seeded in new culture containers, transwells containing LOCs are placed over them to promote their proliferation by the proliferation-enhancing paracrine factors secreted by the LOCs. For all of these cultures, the media are replenished with about 10, 20, 30, 40, 50 or 60%, or more preferentially, 40% conditioned medium in every 2-3 days until a substantial number of clonal colonies of NEECs are grown. These clonal colonies spontaneously form cell clusters that can be harvested and passaged for a further enrichment to increase their propensity toward generating the tissue complex upon differentiation.

There has been a controversy regarding the exact lineages of adult progenitors of islet endocrinal cells (Dor et al., 2004, Nature 429:41-46; Inada et al., 2008, PNAS 105:19915-19919; Xu et al., 2008, Cell 132:197-207). We hold the view that there are adult progenitor cells that can proliferate and generate islet endocrine cells under certain stressful conditions such as culture conditions described in this invention. Several studies have indicated the existence of islet progenitors in postnatal pancreas and in vivo regeneration of endocrinal cells by applying external stresses; for examples, administering toxins such as alloxan or streptozotocin, subjecting pancreas to such surgical treatments as pancreatectomy or tying a pancreatic duct called duct ligation. Recently, the duct ligation was found to render a massive pancreatic inflammation and cell apoptosis followed by the proliferation of an islet progenitor cell population (Xu et al., 2008). The exact tissue localization of the progenitors in the adult pancreatic tissues has not yet been elucidated, but a number of studies have found evidence that they reside in the ductal and/or centroacinar regions of the pancreas, as well as within islets indicated by a few other studies. Recently, certain groups of such progenitor cells were labeled with Aldefluor (Stem Cell Technologies), which utilizes the high enzymatic activity of aldehyde dehydrogenease in progenitor cells (Rovira et al., 2010, PNAS 107:75-80), and were found to be more abundant than previously thought.

The other group of cells to be used for the generation of IPTs is vascular endothelial cells (VECs) normally residing in a continuous vascular system that innervates through the entirety of both islets and pancreatic mesenchyme. These VECs are also isolated from the pancreatic tissue debris that has been collected after 12 to 48 hours of suspension culture for capturing adherent cells or tissues. After a brief expansion of the cells that contain VECs, they are removed from the culture containers, and VECs are purified using anti-CD31 antibody-conjugated magnetic beads (Mylteny Biolgy, Inc.). The purified VECs are further expanded in a serum-containing medium supplemented with endothelial cell growth supplement (EGGS, Sigma-Aldrich Co.). These isolation and culture techniques have been known in the art that enables VEC cultures from various tissues and organ sources.

NEECs and VECs are first in-vitro expanded separately in different culture media before these are mixed by a swirling motion in the presence of calcium ions (1 mM) to promote the generation of spherical tissues. The excess amount of extracellular calcium ions is known to induce the homotypic binding of E-cadherin molecules on the surfaces between adjacent cells, thereby, forming spherical tissues.

Not only a homotypic binding by means of cell surface molecules such as cadherins but also heterotypic cell-to-cell interactions are known to play essential roles during organogenesis of islets. Attention must be paid to the role of VECs particularly in the early developmental stages of islets (Yoshitomi & Zaret, 2004, Development 131:807-817; Lammert et al., 2001, Science 294:564-567). The roles that VECs play with respect to their interactions with the adjacent cells are indeed multifaceted, creating a niche for other types of cells, hence for the term, 'vascular niche' (Nikolova et al., 2007, Trends in Cell Biology 17:19-25). VECs secrete extra-cellular matrices to support the biology of neighboring cells including adhesion, proliferation and functions. Indeed, during islet morphogenesis, pancreatic endocrine progenitor cells adhere and migrate on the extra-cellular matrices by means of a specific set of integrins (Cirulli et al., 2000, Journal of Cell Biology 150:1445-1458). Because β cells even at maturity do not have extra-cellular matrices of their own, their physical integrity is predicted to be dependent on the extra-cellular matrices secreted by the adjacent VECs. After the maturation of islet endocrinal cells, they interact with VECs by possible mechanisms other than gas and/or nutrient exchanges. For example, Johansson et al. (2006, Endocrinology, 147:2315-2324) found a reciprocal enhancement between mature islet cells and adjacent VECs, which secrete HGF to promote the proliferation and maintenance of beta cells, and the latter in turn secrete VEGF to support the former. Although all of these studies may point to the importance of heterotypic cell-to-cell interactions, they have not demonstrated that VECs isolated from pancreatic tissues can promote adult pancreatic progenitors to in vitro differentiate into insulin-producing cells.

There are numerous other studies that describe the roles of cell-to-cell interactions between VECs and beta cells with respect to the VEC-secreted extracellular matrices, and some studies discovered a possible use of such interactions for increasing islet cell functions. For example, Powers et al. (2005, US20050048040A1) attempted to increase the re-vascularization and thereby the functions of mature human islet cells by recombining these with once-dissociated VECs. The functional enhancement of mature islet cells also by means of growth factors and the extra-cellular matrices have often been described in literature, but the enhancement in in vitro differentiation of adult pancreatic progenitor cells into insulin-producing cells has not yet been demonstrated in the context of cell-to-cell interactions with pancreatic VECs.

The in vitro generation of IPTs in our present invention has simulated suspension culture techniques used by a few other studies and demonstrated that resulting islet-like tissues secrete increased amounts of insulin into the surrounding media (Ogata et al., 2004, Endocrine Journal 51:381-386; Todorov et al., 2006). Moreover, the present invention utilizes swirling culture method, in which direct contacts between NEECs and VECs are promoted to increase heterotypic as well as homotypic cell-to-cell interactions for efficient generation of IPTs.

NEECs expanded or passaged are first removed from culture containers by treating them with Accutase (Innovative Cell Technologies, Inc.), a cell-removing enzyme, known to have a minimal damage to mammalian cells. Cells are washed with PBS, inundated with this agent, incubated at RT for 3-10 min., diluted with a medium, removed by gentle pipetting and pelleted by centrifugation at 160×g for less than 4 min. Supernatants are removed, and cell pellets are combined and re-suspended with the IPT-generation medium containing DMEM/Ham's F-12 with 20 mM D-glucose supplemented with 2% (v/v) FCS, 10 mM nicotinamide, 0.1 mM ascorbic acid, and growth factors and mitogens listed in Table 1.

In the mean time, VECs are removed from culture containers in a similar manner, but incubated at 10-15 min. and centrifuged at 300×g for 5 min. Then the NEECs and VECs are mixed in suspension at the respective ratio of 95, 90, 80, or 70% and 5, 10, 20, or 30%, and more preferably 70% and 30%, respectively. A typical cell density in suspension is between any two among $0.1\times$, $0.5\times$, $1.0\times$, $5.0\times$, and $10.0\times10^5$ cells/ml, and more preferably $5.0\times10^5$ cells/ml, and approximately 0.5, 0.75, 1.0 or 1.5 ml, and more preferably 1.0 ml of the cell suspension is loaded into each well of ultra-low adherence 6-well plate (Corning, Inc.). The cell mixture-containing plates are further supplemented with 1 mM $CaCl_2$, placed on an orbital shaker and swirled at a rotation speed of less than 10, 15, 20, or 25 rotations per minute, and more preferably 20 rotations per minute at 37° C. and 5% $CO_2$ for 18 to 24 hours. After this swirl incubation period, the cell typically form tissue spheres of 100-200 micrometer in diameter; then, the medium is completely replenished without $CaCl_2$ and horizontally placed without motion. The culture medium is to be replenished every 1-2 days for the entire maturation period of about 20 days. During this last step of incubation, some of the spherical tissues or IPTs adhere together to form larger tissue clumps, from many of which smaller translucent tissue buds emerge. Tissue spheres formed in this way have significantly smoother surface textures and clearer demarcation of outer tissue membranes than those solely made of NEECs, for which the culture media tend to be contaminated with small cellular fragments which have apparently segregated from the tissue spheres. Thus, the tissue complexes made of NEECs and VECs can maintain their physical integrity, while the tissue spheres made of NEECs alone are more fragile, indicating VECs and/or the matrices secreted by them are likely to increase the physical integrity of the tissue complexes.

Characterization of NEECs and IPTs is routinely performed by such methods as RT-PCR, immunocyto- or immunohistochemistry, and insulin or C-peptide ELISA with respect to their ability of producing and secreting insulin in vitro. C-peptide is examined in case where culture media used contain insulin as a substrate, which makes it difficult to quantify the newly-secreted insulin. In theory equimolar amounts of C-peptide and insulin are produced by a single insulin-producing cell although quantification by ELISA does not necessarily result in paralleled amounts estimated for the two proteins.

Gene expression analyses by RT-PCR are performed in the following method. NEECs or IPTs are removed from the culture media and washed in PBS, and collected cells or tissues are sonicated in a cell-dissolving buffer by a one-second pulse 3 to 4 times. Total RNA is extracted by RNeasy Mini Kit (Qiagen, Inc.) and further purified by RNase-free DNase I Set (Qiagen, Inc.) to remove possible DNA contaminants. Twenty ng of the purified RNA is used as a template to synthesize cDNA using SuperScript III (Invitrogen, Inc.) with random hexamers (Invitrogen, Inc.), and the resulting cDNA is processed with RNase H to remove possible RNA contaminants. Semi-quantitative PCR is performed by Hot-StartTaq PCR reaction mixture (Ambion, Inc.) with 20 ng cDNA template with primers, annealing temperatures, and cycle numbers indicated in Table 2. The PCR products are quantified by the intensity of DNA bands for the designated products' molecular sizes relative to that of the internal control, GAPDH.

Immunocytochemistry is performed in the following method. NEECs are sub-cultured onto collagen I-coated slide chambers with the media of respective stages. The collagen I-coated chamber slides are pre-treated with growth factor or antibodies before used. Once the cells have grown in an appropriate density, they are washed thrice with PBS and fixed in cold methanol for 10 min. or alternatively in 70% ethanol at RT for 30 min., air-dried and washed with PBS and blocked with a blocking solution (Dako, Inc.). The cells are stained with a primary antibody, washed with washing buffer containing PBS with 0.1% BSA and 0.1% Tween20, and incubated with a secondary antibody, followed by DAPI staining in a blocking solution, mounted with VectraShield, and observed under an inverted fluorescent microscope. For immunocytochemistry to detect Ngn3, cultured cells are fixed in 4% paraformaldehyde in phosphate buffer at RT for 10 min, and fixation is quenched with 0.1% glycine solution. Immunological epitopes are unmasked by treating the cells with 0.2% trypsin solution before they are further treated with blocking solution and anti-Ngn3 antibody.

For static incubation to test glucose response of the generated IPTs, approximately 20 IEQs of IPTs or native islets (1 IEQ=1 IPT of 200 micrometer diameter) are loaded in each well of a U-shape bottom 96 well plate with 200 microliter KREBS buffer with 5 mM glucose. The buffer solution is carefully changed afresh by pipetting and incubated at 37° C. and 5% $CO_2$ for one hour (preincubation). Then the IPTs are similarly washed with 200 microliter KREBS buffer with 5 mM glucose and incubated for two hours (Low glucose incubation). After the incubation, the KREBS buffer is collected from the well, washed several times with the same buffer but with 20 mM glucose and incubated for two hours (High glucose incubation). After the incubation, the KREBS buffer is collected and stored at −30° C. until being analyzed. ELISA is performed according to the manufacturers' protocols. The generated IPTs after 20 days of maturation typically secrete insulin up to 10% of that produced by native islets with appropriate degrees of glucose responsiveness.

These and other objects of the present invention are provided by one or more of the embodiments described below.

One embodiment of the invention provides a method of enhancing the formation and endocrinal functions of IPTs by generating in vitro a tissue complex composed of NEECs and VECs. The method allows one to obtain increased amounts of IPTs from given cell sources, and IPTs are endowed with increased endocrinal functions with regard to insulin secretion.

In another embodiment of the method of enhancing the formation and endocrinal functions of IPTs, both the NEECs and VECs can be isolated from the same postnatal mammalian pancreas, and the latter also from other somatic tissues.

The NEECs are the cells residing in the pancreatic ducts and/or centroacinar cells but lack secretion of insulin or other endocrine hormones.

In another embodiment of the method of enhancing the formation and endocrinal functions of IPTs, NEECs can be obtained from the pancreatic discards which are the tissue remains after enzymatic digestion of pancreas and subsequent removal of islets.

One embodiment of the invention provides a method of in vitro culture of said NEECs that includes a cell-capturing step by seeding said pancreatic discards in RPMI1640 containing 10% (v/v) FCS in culture containers coated with 0.2 mg/ml rat tail collagen I and further coated with anti-E-cadherin antibody and anti-c-Met (HGF receptor) antibody with concentration ranging between 1:100 and 1:1000. The tissues are cultured preferably at around 37° C. and around 5% $CO_2$ for 24 to 36 hours.

Another embodiment of the invention provides a method of in vitro culture of NEECs that includes a colony induction step by changing the medium in the cell-capturing step to a serum-free medium containing 1 g/L ITS (5 microgram/ml insulin, 5 microgram/transferrin, 5 ng/ml sodium selenite), 20 ng/ml recombinant human FGF-2 and 1400 U/ml recombinant human LIF in DMEM/Ham's F-12 containing 7 mM D-glucose and cultured for at least 24 hours.

A further embodiment of the invention provides a method of in vitro culture of NEECs that includes an initial colony-growing step by changing the medium in the colony induction step to another serum-free medium containing 1 g/L ITS, 0.2% BSA, 10 mM nicotinamide, and 10 ng/ml recombinant human KGF in DMEM/Ham's F-12 containing 7 mM D-glucose and cultured for at least 5 to 7 days. The medium preferably contains 0.02 micromolar 2-mercaptoethanol in later stages of culture in order to inhibit the growth of fibroblastic cells that may prevent the growth of NEECs and mycoplasma-removing agents to inhibit the possible mycoplasma infestation. The media are replenished in every 2-3 days until a substantial number of clonal colonies of NEECs with the size ranging 10-30 micrometer in diameter emerge.

One embodiment of the invention provides a method of passaging NEECs for their selective expansion that includes a cell-removal step by removing NEECs from the culture containers by treating them with a tissue-digesting enzyme, Accutase. The removed cells are centrifuged at or below 160×g for less than 4 min.

Another embodiment of the invention provides a method of passaging NEECs for their selective expansion that includes a culturing step where the removed cells in the previous step are seeded on the same culture container as in the previous step but pretreated with anti-Notch 1 antibody with the final concentration of 1:100 to 1:1000 in the same medium but with 0.1 micromolar atorvastatin and cultured. The media are replenished with 40% conditioned medium in every 2-3 days until a substantial number of clonal colonies of NEECs are grown.

In another embodiment, alternatively, the collagen coating is prepared without KGF or anti-Notch 1 antibody, and KGF in the culture medium of the initial colony-growing step (3) is replaced with 10, 15, 20 and 30, and more preferably, 20 ng/ml HGF, 10, 15, 20, 30, 40 and 50, and more preferably, 40 ng/ml EGF and 2, 4, 8, 14, 20, 25, and more preferably 4 micromolar rock inhibitor. 0.01-1.0 micromolar, more preferably 0.03-0.3 micromolar, for example, 0.1 micromolar atorvastatin and 10, 15, 20 and 30, and more preferably 20 ng/ml BMP4 or BMP7 to enrich NEECs in the propensity toward becoming endocrinal cells upon differentiation later.

In a further embodiment of the invention, epithelial cell clumps which are left adhering to culture containers after NEECs have been removed by Accutase treatments, thus called "left-over cells (LOCs)," are then removed from the culture containers with 0.05% trypsin-EDTA at 37° C. for 5 min, washed with the serum-free medium, transferred into transwells and placed in the medium for enhancing the proliferation of the NEECs.

In a further embodiment of the invention, NEECs cultured with LOCs in transwells form cell clusters, which can be passaged for a further enrichment to increase their propensity toward forming the tissue complex upon differentiation.

In one embodiment of the invention, cultured NEECs can be characterized by cells that express the transcription factor, Hes1, a downstream target of Notch signaling, and Ngn3 upon treatment with all-trans retinoic acid and cyclopamine KAAD, thereby, signifying the identity as progenitors competent for generating insulin-producing cells.

One embodiment of the method of isolating and culturing VECs includes a step to isolate VECs from the pancreatic discards or floating tissue debris that has been collected from the pancreatic discard cultures. This is to seed the tissue discards or floating tissue debris in RPMI1640 containing 70-100 microgram/ml EGGS and 20% (v/v) FCS, which has been heat-inactivated at 65.5° C. for 60 to 70 min., in culture containers coated with 1.8 mg/ml rat tail collagen I. The culture medium containing non-adherent cells and tissues after 18 hours of culture is replaced with a fresh medium.

In one embodiment of the method of isolating and culturing VECs, VECs can be purified by using antibody-conjugated microbeads and an anti-CD31 antibody, and subsequently expanded with the procedures described in the previous step.

In a further embodiment of the method of isolating and culturing VECs, VECs are either derived from the same donor tissues from which NEECs are isolated or tissues of the recipient to which said IPTs are to be transplanted for the purpose of possible attenuation of immunological rejections.

One embodiment of the invention provides a method of generating a tissue complex of NEECs and VECs in a low adherence culture container; the two kinds of cells preferably have mixing ratios of cell numbers of 95, 90, 80, or 70% and 5, 10, 20, or 30%, respectively. The tissue complex is generated by a slow swirling motion of the container preferably at less than 10, 15, 20 or 25 rpm, at around 37° C. and enhanced $CO_2$ such as 5% $CO_2$ for 18 to 24 hours.

Another embodiment of the invention provides a method of generating a tissue complex in a culture medium such as a medium containing DMEM/Ham's F-12 with 20 mM D-glucose supplemented with 2% (v/v) FCS, 2 ng/ml Activin A, 5 ng/ml Betacellulin, 20 ng/ml HGF, 20 ng/ml Gastrin, 20 ng/ml IGF-1, 5 ng/ml KGF, 20 ng/ml VEGF, 20 ng/ml BMP7.20 ng/ml Exendin-4, 10 mM nicotinamide, 0.1 mM ascorbic acid and 1 mM $CaCl_2$ until spherical clusters of IPTs appear in the medium during the swirling motion of the container.

A further embodiment of the invention provides a method of maturing said IPTs with the same methods except for the culture container horizontally placed without motion and culture medium without $CaCl_2$. The culture medium is to be replenished every 1-2 days for the entire maturation period of about 20 days.

A further embodiment of the invention provides a method that the VECs are seeded on culture containers to produce a near-confluent monolayer in the medium specified in the fourth preferred embodiment, then cells or cell clusters dissociated from isolated and purified native islets are seeded on the VEC monolayer to enhance the cells or cell clusters of the islets to proliferate.

In one embodiment of the invention of the method of generating IPTs, the IPTs thus generated comprise a greater number of tissues than those without the method.

In another embodiment of the invention of the method of generating IPTs, the IPTs thus generated comprise cells that produce more insulin than those without the method.

In another embodiment of the invention of the method of generating IPTs, the functions of IPTs thus generated comprise the secretion less than 5%, 10%, 40%, 60%, 80% or 100%, and for example, around 10% of insulin produced by con-specific native islets.

In a further embodiment of the invention of the method of generating IPTs, the functions of IPTs comprise greater glucose-responsiveness in insulin secretion than that without the method.

In a further embodiment of the invention, cells or cell clusters dissociated from isolated and purified native islets and seeded on the VEC monolayer are enhanced of proliferation compared with those seeded on substrates without VECs.

In a further embodiment of the invention, antibiotics to be added to the culture media are 50-100 U/ml penicillin and 50-100 microgram/ml streptomycin, or streptomycin may be replaced with 50-100 U/ml gentamycin.

TABLE 1

Growth factors used for culturing NEECs, VECs and IPTs

| Growth factors | Manufacturer | Product No. | Concentration |
|---|---|---|---|
| rh FGF-2 | PeproTech | 100-18B | 20 ng/ml (NEECs) |
| rh LIF | Chemicon | LIF2010 | 1400 U/ml (NEECs) |
| rh KGF | Wako Chemicals | 119-00661 | 10 ng/ml (NEECs); 5 ng/ml (IPTs) |
| rh EGF | PeproTech | AF-100-15 | 40 ng/ml (NEECs) |
| rh BMP4 | R&D | 314-BP-010 | 10 ng/ml (NEECs) |
| rh BMP7 | R&D | 354-BP-010 | 20 ng/ml (NEECs, IPTs) |
| ECGS | Sigma-Aldrich | E2759 | 100 µg/ml (VECs) |
| rh Activin A | PeproTech | 120-14 | 2 ng/ml (IPTs) |
| rh HGF | PeproTech | 100-39 | 20 ng/ml (NEECs, IPTs) |
| rh Gastrin | GenScript | RP12740 | 20 ng/ml (IPTs) |
| rh Betacellulin | PeproTech | 100-50 | 5 ng/ml (IPTs) |
| rh IGF1 | R&D | 291-G1 | 20 ng/ml (IPTs) |
| rm VEGF | BioSource | PMG0114 | 20 ng/ml (IPTs) |
| rh Exendin4 | Sigma-Aldrich | E7144 | 20 ng/ml (IPTs) | rh: recombinant human;
mh: recombinant murine;
parentheses specify types of cells or tissues applied.

TABLE 2

Table 2. Primer pairs used for PCR

| Gene name | Sequence | Size (bp) | T (° C.) | Cycles |
|---|---|---|---|---|
| Ngn3 (F) | CAGTCACCCACTTCTGCTTC | 159 | 45 | 40 |
| Ngn3 (R) | CAGTCACCCACTTCTGCTTC | | | |
| Pdx1 (F) | CCACCCCAGTTTACAAGCTC | 324 | 49 | 35 |
| Pdx1 (R) | TGTAGGCAGTACGGGTCCTC | | | |
| NeuroD (F) | GTCCCAGCCCACTACCAATT | 440 | 49 | 35 |
| NeuroD (R) | CGGCACCGGAAGAGAAGATT | | | |
| Ptf1a (F) | AACCAGGCCCAGAAGGTTAT | 150 | 45 | 30 |
| Ptf1a (R) | CCTCTGGGGTCCACACTTTA | | | |
| Notch1 (F) | TTACAGCCACCATCACAGCCA | 376 | 49 | 35 |
| Notch1 (R) | ATGCCCTCGGACCAATCAGA | | | |
| Hes1 (F) | TCAACACGACACCGCACAAACC | 270 | 54 | 35 |
| Hes1 (R) | GGTACTTCCCCAACACGCTCG | | | |
| HNF6 (F) | GCAATGGAAGTAATTCAGGGCAG | 461 | 49 | 35 |
| HNF6 (R) | CATGAAGAAGTTGCTGACAGTGC | | | |
| Nkx6.1 (F) | CCGGTCGGACGCCCATC | 467 | 54 | 35 |
| Nkx6.1 (R) | GAGGCTGCCACCGCTCGATTT | | | |

TABLE 2-continued

Table 2. Primer pairs used for PCR

| Gene name | Sequence | Size (bp) | T (° C.) | Cycles |
|---|---|---|---|---|
| Ins1 (F) | GCTGGTAGAGGGAGCAGATG | 347 | 49 | 35 |
| Ins1 (R) | CAGAGACCATCAGCAAGCAG | | | |
| Ins2 (F) | CCCTGCTGGCCCTGCTCTT | 212 | 51 | 35 |
| Ins2 (R) | AGGTCTGAAGGTCACCTGCT | | | |
| GAPDH (F) | AACTTTGGCATTGTGGAAGG | 223 | 49 | 30 |
| GAPDH (R) | ACACATTGGGGGTAGGAACA | | | |

(F) and (R) signify forward and reverse sequences, respectively.

DEFINITIONS

The term "pancreas" or "pancreata" is in art recognized as and referred to a both endocrine and exocrine organ located in an abdominal cavity between the spleen and duodenum of the mammalian organisms.

As used herein, "pancreatic islets" refer to the small tissue clusters in a pancreas that secrete endocrinal hormones such as insulin, glucagon, somatostatin, pancreatic polypeptide and herein.

As used herein, "pancreatic discards" refer to the pancreatic tissues left after the removal of islets from pancreas. In clinical islet transplantation, donor pancreatic tissues are processed by collagenase digestion and a series of subsequent purification steps to collect islet tissues, producing a huge amount of pancreatic discards as byproducts. It has been said and attempted that islet progenitor cells possibly residing in them could be utilized for cell therapy to cure diabetes.

As used herein, "non-endocrinal epithelial cells (NEECs)" refer to the cells that have been isolated from a postnatal mammalian pancreas and are composed of heterogeneous cells within a larger category of epithelial cells that include progenitors not yet having attained endocrinal functions. NEECs thus contain cells capable of proliferating and generating insulin-producing tissues (IPTs) in vitro. The NEECs possibly reside in a ductal portion of the pancreas and/or can be synonymous with centroacinar cells as they can be characterized as Aldefluor positive cells.

As used herein, "left-over cells (LOCs)" refer to epithelial cells tightly attaching together forming cell clumps which remain after the initial removal of NEECs from culture containers for passaging. These cells proliferate rapidly under the herein-described culture conditions and are possibly progenitors of acinar cells, duct cells and/or those de-differentiated to have duct-like or duct-progenitor-like phenotypes. These cells enhance the proliferation of the NEECs supposedly by secreting some unidentified paracrine factors.

As used herein, the term, "vascular endothelial cells (VECs)" refers to the vascular endothelial cells isolated from a postnatal mammalian pancreas. VECs can also be obtained from either bone marrow cells or peripheral blood. VECs are derived from the same donor, from which NEECs are isolated, or more preferably from a recipient to which IPTs are to be transplanted.

As used herein, the term, "insulin-producing tissues (IPTs)," refers to a group of cells forming spherical tissue complex, which can be generated in vitro and matured as endocrinal tissues that can secrete insulin and possibly other endocrinal hormones.

As used herein, "generation" or "generating" refers to a tissue-forming process in which cells that can be categorized as NEECs undergo a change to become tissue complex that can meet the definitions of IPTs. Thus, NEECs under the influence of culture conditions described in the present invention change to become or "generate" IPTs.

As used herein, "progenitor cells" refer to cells which have been selectively cultured from pancreatic discards allowed to proliferate and be passaged under the conditions specified in the invention and which can be characterized as having a competence to become pancreatic endocrinal cells and identified as Ngn3-positive cells upon treatment with all-trans retinoic acid and cyclopamine KAAD.

As used herein, "culturing" refers to propagating or nurturing a cell, clusters of cells, a tissue complex or native pancreatic islet cells, by incubating in an environment that allows for cell proliferation or generation of functional tissues. Culturing requires media containing appropriate growth factor, mitogens and/or differentiation factors that generally support the growth and/or functional maturation of the cell, clusters of cells, a tissue complex or native pancreatic islet cells to be cultured.

As used herein, "tissue complex" refers to a composition of two groups of cells obtained for the purpose of generating insulin-secreting tissues (IPTs). A tissue complex is formed by allowing these cells of given mixing ratios in a low adherence culture container with a slow swirling motion. The tissue complex can be incubated in a herein-described serum-free medium supplemented with 1 mM $CaCl_2$. The calcium ions in the medium activate cadherin molecules between adjacent cells thereby promote the cell-to-cell attachment, thus forming a tissue complex.

The practice of the present invention employs, unless otherwise indicated, conventional techniques of cell biology, cell culture, molecular biology, microbiology, recombinant DNA, which are within the skill of the art. These techniques are described in the literature; for examples, Basic Manuals for Molecular Biology, Book 3 "Truly-Amplifying PCR" (Yodo Publishing, Inc., 2004); Culture of Animal Cells (R. I. Freshney, Alan R. Liss, Inc., 1987); Immunocytochemical Methods and Protocols, Vol. 115 in Methods in Molecular Biology (Lorette C. Javois, eds., Humana Press, Totowa, N.J., 1994); The ELISA Guidebook (Methods in Molecular Biology) by Crowther (Humana Press, 2000); Methods in Cell Biology, Vol. 41, Flow Cytometry, $2^{nd}$ Ed., ed. By Darzynkiewicz, Robinson and Crissman (Academic Press: 1994).

EXAMPLES

Details of the experimental procedures used to generate the results of the following analyses are described in corresponding EXAMPLES. Error bars indicated in the graphs represent standard deviations for the following figures. Each of photograph images in the drawings is converted from a color image by image conversion into a gray-scale one, or by RGB-color separation and taking one among red, green and blue color-separation images.

Example 1

Collection of Pancreatic Discards

Murine pancreata (C57Bl/6) were harvested immediately after injecting intra-ductally into them 2.0 to 2.5 ml 0.1% Collagenase S-1 (Nitta Gelatin, Inc.) in HBSS (Sigma-Aldrich Co.). These pancreata were incubated in HBSS at 37° C. for 20 min, cooled on ice and shaken vigorously for 20 seconds with additional 10 ml RPMI1640 (Invitrogen, Co.) with no additives. The collagenase-digested pancreatic tissues were then passed through a 1.0 mm steel mesh to remove large clumps of debris which were mostly fats and connective tissues. The pancreatic elutes were then thrice washed with 50 ml RPMI1640 by centrifuging at 250×g at 4° C. for 2 min. Approximately 1 ml of the tissue pellet was re-suspended with a 15 ml mixture of M-Kyoto solution (Ohtsuka Pharmaceutical Co.) and Optiprep (Axis-Shield, PoC AS, Oslo, Norway) with a density adjusted at 1.1 g/ml into a 50 ml conical tube. Then, the suspension was gently overlaid with 15 ml of another mixture with a density adjusted at 1.077 g/ml, and further with 5 ml of RPMI1640. The layered suspensions were centrifuged at 400×g at 4° C. for 20 min. A middle opaque layer which contained mostly islets was removed by careful pipetting to be used for native islet cell proliferation test in EXAMPLE 14, and the rest of the suspended cells and tissues and tissue debris at the bottom were collectively identified as "pancreatic discards," and subjected to the cell-capturing step.

Example 2

Cell Capturing of Non-Endocrinal Epithelial Cells (NEECs)

The pancreatic discards were twice washed with 50 ml RPMI1640 by centrifuging at 250×g at 4° C. for 2 min and either immediately seeded with a serum-containing medium, RPMI1640 supplemented with 10% heat-inactivated FCS (HyClone Laboratories, Inc.) and PenStrep (Penicillin/streptomycin in final concentration=50/50, Wako Chemicals Co.) on 6-well plates or 10 cm dishes (Greiners Inc.). Alternatively, the tissue clumps of the pancreatic discards were further dissociated with Accutase (Innovative Cell Technologies, Inc.) at RT for 10 min. The pancreatic digests from approximately one pancreas were seeded into each plate or dish. For the purpose of capturing NEECs, the plate or dish was pre-coated with 0.2-0.25 mg/ml rat tail collagen I (BD Biosciences) at RT for 1 hour and further coated with anti-mouse E-cadherin antibody (Clone: 36/E-Cadherin, BD Biosciences) and/or anti-c-Met (HGF receptor) antibody (Wako Chemicals, BAF527) with concentrations ranging between 1:100 and 1:1000 at RT for 1 hour. The tissues were cultured at 37° C. and 5% $CO_2$ for 24 to 36 hours. During this period, floating tissue debris was once removed along with the culture medium and a fresh serum-containing medium was added. FIG. 1A is a microscopic image showing thus obtained cells remained adhering on the collagen I-coated dish surface when only the anti-c-Met is used as antibody coated on the dish surface. FIG. 2A is a graph showing numbers of thus obtained cells adhering on the surfaces when the NEECs were cultured for 18 and 36 hours in presence of E-cadherin ("Ecad") and/or anti-c-Met ("cMet") antibody or in absence of antibody (Two-way ANOVA: effect=between antibody treatments, F=11.6, n=6/group, p=0.0003; effect=18 hours vs. 36 hours cultures, F=87.7, n=6/group, p<0.0001).

Example 3

Colony Induction for NEECs

After the cell capturing step, the medium was removed alter a gentle swirling of the plates that allowed some larger tissue clumps to be released from the coated surface. To induce clonal colony growth of NEECs, the culture was added with a serum-free medium containing 1 g/ml ITS (final concentrations: 5 microgram/l insulin, 5 microgram/l transferrin, 5 ng/l sodium selenite) (MP Biomedicals, LLC.), 0.2% BSA (Sigma-Aldrich Co.), 20 ng/ml recombinant human FGF-2 and 1400 U/ml recombinant human LIF in DMEM/Ham's F-12 containing 7 mM D-glucose (Wako Chemicals Co.), PenStrep (50/50) and Cycline B1 (Roche Pharmaceutical, Inc.), and cultured at 37° C. and 5% $CO_2$ for at least 24 hours. FIG. 1B shows a microscopic image of thus induced cell colonies. For comparison, same procedures from Examples 1 and 2 and above induction step were made for tissues obtained only from ductal part of the same pancreas ("Ductal tissues"), instead of its whole part ("All tissues") as in Example 1; and also made were same procedures except for the medium omitted with the human FGF-2 at the induction step. Results are shown in FIG. 2B (Two-way ANOVA: effect=FGF-2 treatment vs. control, F=75.9, n=6/group, p<0.0001; effect=ductal tissues vs. all tissues, F=338.0, n=6/group, p<0.0001). Including FGF-2 into this induction step with the serum-free medium yielded more NEECs than with the medium including no FGF-2, and the whole pancreatic discard tissues yielded more NEECs than the ductal tissues which were hand-picked by pipetting before seeded.

Example 4

Initial Colony Expansion for NEECs

To expand NEEC colonies, after the colony induction step (EXAMPLE 3), the serum-free medium was replaced with another serum-free medium containing 1 g/L ITS, 0.2% BSA, 10 mM nicotinamide, and 10 ng/ml recombinant human KGF in DMEM/Ham's F-12 (1:1 mixture) containing 7 mM D-glucose, PenStrep (50/50), 0.02 micromolar 2-mercaptoethanol and Cycline B1, and cultured for two days (FIG. 1C). Then the media were subsequently replenished without Cycline B1 but with 40% conditioned medium in every 2-3 days until a substantial number of clonal colonies of NEECs with the size ranging 10-30 micrometer in diameter grew for a period of 2-7 days (FIG. 1D).

Example 5

Passaging and Selective Expansion of NEECs

NEECs after the initial growth step of EXAMPLE 4 were washed twice with PBS and removed from the plates by treating the cells with Accutase at RT for 5 min. The removed cells were filtered through a 40 micrometer nylon mesh and centrifuged at or below 160×g for less than 4 min. The cell clusters remaining on the plates, left-over cells (LOCs), were kept incubated with the same serum-free medium in a separate container to be used later for transwell culture in EXAMPLE 6. The cell pellet was re-suspended with the same serum-free medium as in EXAMPLE 4 but further supplemented with 0.1 micromolar atorvastatin (LKT Laboratories, Inc.). The cells with this suspension medium were seeded on 6-well plates, 10 cm dishes or 4-well slide chambers (Biocoat Cellware, BD Labware) coated with rat tail collagen I as in EXAMPLE 2, but the collagen solution for coating the plates contained 10 ng/ml KGF, and the coated surface was further treated with anti-mouse Notch 1 antibody (Clone: 8G10, Millipore) with the final concentration of 1:100 to 1:1000. The media were replenished with 40% conditioned medium in every 2-3 days until a substantial number of clonal colonies of NEECs were grown. In a comparative experiment, the anti-mouse Notch 1 antibody was omitted in otherwise same procedures from EXAMPLE 1 through just above. FIG. 2C (Unpaired t-test, n=5/group, p<0.0001) shows percentages of bromodeoxyuridine-positive (Brdu+) cells passaged onto anti-Notch1 antibody-treated collagen I-coated culture containers ("Anti-Notch1") and those onto untreated collagen I-coated culture containers ("Untreated"). The immunocytochemistry was performed by the same method as that in EXAMPLE 4. As shown in FIG. 4, the proportions of Brdu+ cells indicating proliferation were approximately twice for "Anti-Notch1" compared with those for "Untreated".

Example 6

Cultures of NEECs Using Modified Serum-Free Media and LOCs with Transwells

NEECs after the Selective Expansion of Example 5 were passaged onto collagen I-coated 12-well transwell plates (Millipore Co.) in a modified serum-free medium containing DMEM/Ham's F-12 with 7 mM D-glucose, PenStrep (50/50), 0.02 micromolar 2-mercaptoethanol, ITS (5 microgram/ml insulin, 5 microgram/ml transferrin, 1.25 ng/ml sodium selenite), 0.2% BSA, 10 mM nicotinamide, 20 ng/ml HGF, 40 ng/ml EGF, 20 ng/ml BMP7 and 4 micromolar rock inhibitor (Y-27632. 2HCl) and incubated with hanging transwell inserts (a kind of container having a porous bottom overlaid to and distanced from the culture on bottom of the transwell plate) to which clumps of left-over cells (LOCs) were placed, for three days. Then, microscopic images were taken for the NEECs on the coated surface of the culture container (i.e., on the bottom of the transwell plate, or in the "lower compartment"), which are shown in FIG. 3-1A; and for the LOCs in the transwell inserts (i.e., on bottom of the transwell inserts, or in the "upper compartment") as shown in FIG. 3-1B. NEECs grown in this manner often formed cell clusters (FIG. 3-1A, arrows), which grew in size for the period of one week (FIG. 3-1C). As indicated by arrows in FIG. 3-1A and FIG. 3-1B, NEEC clusters in the lower compartment roughly align in positions in culture with LOC clusters in the transwell insert at above, which suggests that some paracrine factors secreted from the LOC clusters physiologically and/or cell-biologically influence the NEECs in the vicinity. When NEECs grown in with LOC in this manner, the number of NEEC clusters significantly increased as compared with that of the control without LOCs (FIG. 3-2, Unpaired t-test, n=3 groups/treatment, t=0.0021). FIG. 3-3 indicates mRNA expressions of Pdx-1 and Ins1 from these cells examined by semi-quantitative RT-PCR. While LOCs showed a strong signal of Pdx-1 in even greater magnitude than that of the native islets, NEECs showed only a moderate signal. Contrastingly, upon differentiation, LOCs showed no signal of Ins1 as opposed to NEECs. Note that NEECs cultured with LOCs in inserts ("NEECs+FLOC") showed the Ins1 signal in a greater extent than NEECs without LOCs. ("NEECs−LOC")

Example 7

Cultures of NEECs Enriched for Progenitors that Differentiate into Insulin-Producing Cells NEECs after the Selective Expansion of Example 5 were sub-cultured onto collagen I-coated slide chambers (Biocoat Cellware, BD Labware) and incubated in the same serum-free medium as in EXAMPLE 4 but with 0.1 micromolar atorvastatin (ATS) for 5 days. In a "Control", the atorvastatin is omitted, thus, the medium being exactly the same as that in EXAMPLE 4 was used. These cells were subsequently induced of differentiation for 3 days by changing the medium with DMEM/Ham's F-12 (1/1) having; 20 mM D-glucose, 2% (v/v) FCS, 2 ng/ml Activin A, 5 ng/ml Betacellulin, 20 ng/ml HGF, 20 ng/ml Gastrin, 20 ng/ml IGF-1, 5 ng/ml KGF, 20 ng/ml BMP7, 20 ng/ml VEGF, 20 ng/ml Exendin-4, 10 mM nicotinamide and 0.1 mM ascorbic acid. For immunocytochemistry, cells were fixed in cold methanol and blocked with a blocking solution ("Peroxidase Blocking Reagent" of Dako NS, containing hydrogen peroxide and 15 mM sodium azide.) at RT for 1 hour, and treated with anti-insulin antibody (Millipore International, Inc., Linco 4011-01F) (1:400) at RT for 30 min., washed with blocking solution and treated with Cy3-conjugated secondary antibody (Anti-Guinea Pig IgG) (1:800). Nuclei were stained with DAPI, and the slides were mounted with VectraShield (trade name of an antifade solution of Vector Laboratories) and observed under fluorescent microscope (FIG. 4A). The percentage of insulin-positive cells was calculated relative to the number of DAPI-stained nuclei indicating the total number of cells in a given field of observation (FIG. 4B). As shown in FIG. 4B, percentage of insulin-positive cells was significantly greater for the ATS-treated cells than for the control cells (Unpaired t-test: n=7/group, p<0.0001).

Example 8

Identification of NEECs as Progenitors Competent for Generating IPTs

NEECs after the enrichment and differentiation of Example 7 were sub-cultured into collagen I-coated slide chambers (Biocoat Cellware, BD Labware) and incubated with or without 2 micromolar all-trans retinoic acid (Wako Chemicals Co.) and 0.25 micromolar cyclopamine KAAD (Merk Ltd.) in the same serum-free medium as in EXAMPLE 4 but without KGF nor atorvastatin for at least 24 hours. These NEECs were then subjected to the analyses of immunocytochemistry. The NEECs were fixed with 4% paraformaldehyde (Wako Chemicals Co.) in phosphate buffer solution of pH=7.4 at RT for 30 min, and the fixative was quenched with 100 mM glycine in PBS. Immunological epitopes were unmasked by treating the cells with 0.05% trypsin in 1% $CaCl_2$ solution at 37° C. for 10 minutes. The cells on the slides were treated with blocking solution ("Peroxidase Blocking Reagent" of Dako, Inc.) and anti-Ngn3 antibody (Millipore International, Inc., AB5684) (400:1) and FITC-conjugated secondary antibody (800:1), followed by observation by a fluorescent microscope (FIG. 5A). Immunocytochemical images were analyzed by color transformation by Adobe Photoshop (version 6), and cells showing color intensities above an arbitrarily-selected threshold level were designated as Ngn3-positive. Thus obtained percentages of the Ngn3- positive cells within the NEECs are shown in FIG. 5B. NEECs treated with all-trans retinoic acid and cyclopamine KAAD ("Cycl-K+RA") showed a significantly greater proportion of Ngn3-positive cells than those untreated ("Control") (n=3 cell samples per treatment, p<0.0001; Unpaired Student-t test).

Example 9

Gene Expression Analyses

Semi-quantitative RT-PCR was performed to characterize the expressions of mRNAs associated with islet endocrine progenitors and insulin-producing tissues as well as native islets isolated from a C57BI/6 mouse: Ngn3, Pdx1, NeuroD, Ptf1a, Notch1, Hes1, HNF6, Nkx6.1, Ins1 and Ins2. Total RNA was extracted from $1.0 \times 10^5$ cells by RNeasy Mini Kit (Qiagen, Inc.), and possible DNA contaminants were removed by RNase-free DNase I Set (Qiagen, Inc.). Reverse transcription was performed with 20 ng of RNAs by Super Script III (Invitrogen, Inc.) with random primers (Invitrogen, Inc.), and synthesized cDNA were treated with RNase H (Wako Chemicals Co.) to remove any RNA contaminants. PCR was performed with 20 ng cDNA by using Hot Start Taq Master Mix (Promega Co.) with given pairs of primers, annealing temperatures, and cycle numbers listed in Table 2. Amplified PCR products were analyzed by gel-electrophoresis with 2% agarose gel and 0.001% ethydium bromide (FIGS. 6A, 6B, 9A-9C). In the FIGS. 6A-6B, the numbers 1-4 indicate the tissues or cell cultural samples used for the analyses: "1", pancreatic discards of Example 1; "2", NEECs after 5 days of culture in serum-free media with atorvastatin (ATS), of Example 7; "3", NEECs subsequently cultured with media containing all-trans retinoic acid and cyclopamine KAAD for 24 hours, of Example 8 ("Cycl-K$^+$ RA" of FIGS. 5A-5B); and "4", NEECs culture control of "3", that is, "Control" of Example 8 and FIGS. 5A-5B. Arrows in the FIGS. 6A-6B highlight that Ngn3 and Hes1 expressions are apparently synchronized, indicating subpopulations of the cells undergo a slightly different time course in their generation of endocrine progenitors.

Example 10

Isolation and Culturing of VECs

Figures 1, 7:
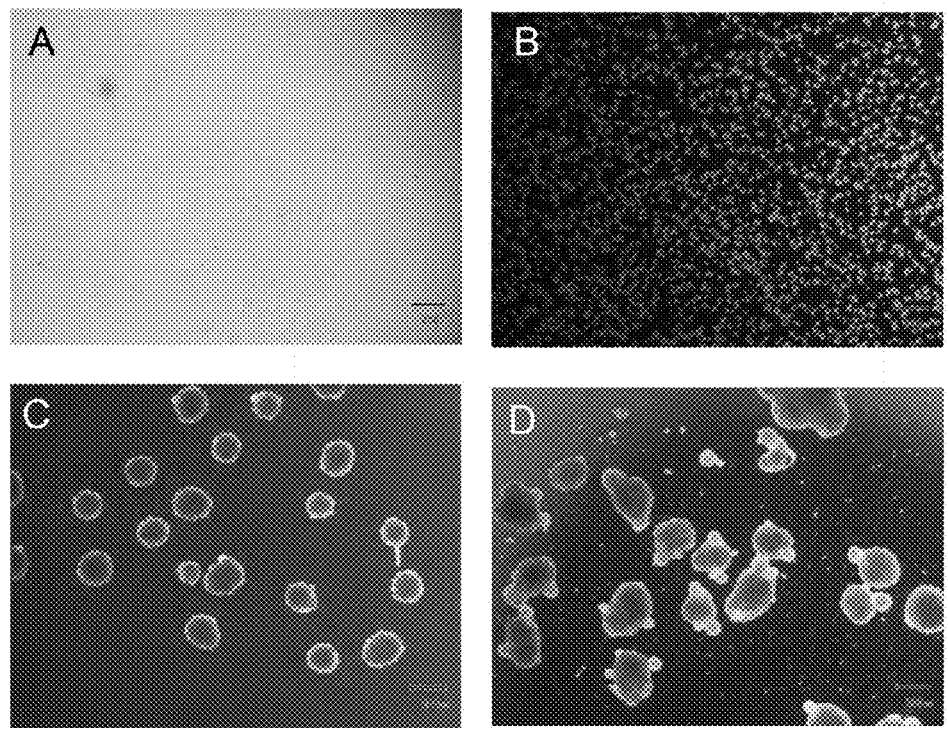
FIG. 7-1 shows the images of cells used for generating IPTs (panels "A" and "B"), and generated IPTs (panels "C" and "D"), where the panel "A" shows VECs that were grown from pancreatic debris, isolated by magnetic microbeads using anti-CD31 antibody and expanded, where the panel "B" shows mixed cell suspension consisting of 80% NEECs and 20% VEC in IPT-generating medium prior to incubation, where the panel "C" shows spherical tissue complexes after incubation of the mixed cell suspension with a swirling motion for 24 hours, and where the panel "D" shows IPTs in maturation.

The floating tissue debris removed from the culture of pancreatic discards in EXAMPLE 2 were seeded with RPMI1640 containing 100 microgram/ml EGGS and 20% (v/v) FCS, which had been heat-inactivated at 65.5° C. for 60 to 70 min., in 24 well plates coated with 1.8 mg/ml rat tail collagen I. The non-adherent tissue debris after 18 hours of culture was removed and briefly washed with PBS before replenished with a fresh medium containing 0.1% (v/v) fungizon (Sigma-Aldrich Co.) and cultured for 7-10 days. The cells were then removed by Accutase treatment, and suspended cells were purified by antibody-conjugated magnetic microbeads (Miltenyi Biotec, Inc.) and an anti-CD31 antibody (Pharmingen, Co.). The cell eluates were cultured with the same medium, in which the cells were removed as just above, in collagen I-coated T25 flasks (Corning, Inc.). An image of thus obtained suspension of the cells (VECs) is shown in FIG. 7-1A.

Example 11

Formation of Tissue Complex

NEECs after the enrichment and differentiation of Example 7 and VECs after the culturing of Example 10 were removed from respective container surfaces by Accutase treatments and mixed together with the ratios of cell numbers: 95/5, 90/10, 80/20, and 70/30, respectively. FIGS. 7-1B to 7-1D and 7-2 show results when the ratio is 80/20, which seems to be optimum in view of enhancing function of the tissue complex and in view of not so decreasing ratio of the NEECs. The ratio of the cell mixture suspension was seeded on the ultra low adherence 6-well plate (Costar 3471, Corning, Inc.) with a tissue-generation medium (FIG. 7-1B). The medium contains DMEM/Ham's F-12, 20 mM D-glucose, 2% (v/v) FCS, 2 ng/ml Activin A, 5 ng/ml Betacellulin, 20 ng/ml HGF, 20 ng/ml Gastrin, 20 ng/ml IGF-1, 5 ng/ml KGF, 20 ng/ml BMP7, 20 ng/ml VEGF, 20 ng/ml Exendin-4, 10 mM nicotinamide, 0.1 mM ascorbic acid and 1 mM $CaCl_2$. The cell mixture suspension was subjected to a slow swirling motion of about 20 rotations/min at 37° C. and 5% $CO_2$ for 18 to 24 hours until spherical clusters of IPTs were generated (FIG. 7-1C). The IPTs were allowed to mature with the same methods as just above except for the culture container horizontally placed without motion and culture medium without $CaCl_2$. The culture medium was replenished every 1-2 days for the entire maturation period of about 20 days (FIG. 7-1D). As seen from panels "C" and "D" of FIG. 7-1, smaller tissue parts budded out, while some IPTs merged to form larger tissue clumps, on course of maturation of IPTs. For comparison, NEECs after the enrichment and differentiation of Example 7 without mixing with VEC were subjected to the culturing described above. Numbers of IPTs having 100-200 micrometer diameter generated either from NEECs alone or a tissue complex of NEECs and VECs were measured and shown in FIG. 7-2 (Unpaired t-test, n=3 groups of incubated cells, p<0.0001). As seen from FIG. 7-2, number of the IPTs from the tissue complex was more than three times of that from NEECs alone.

Example 12

Characterization of IPTs

Figures 2, 7:
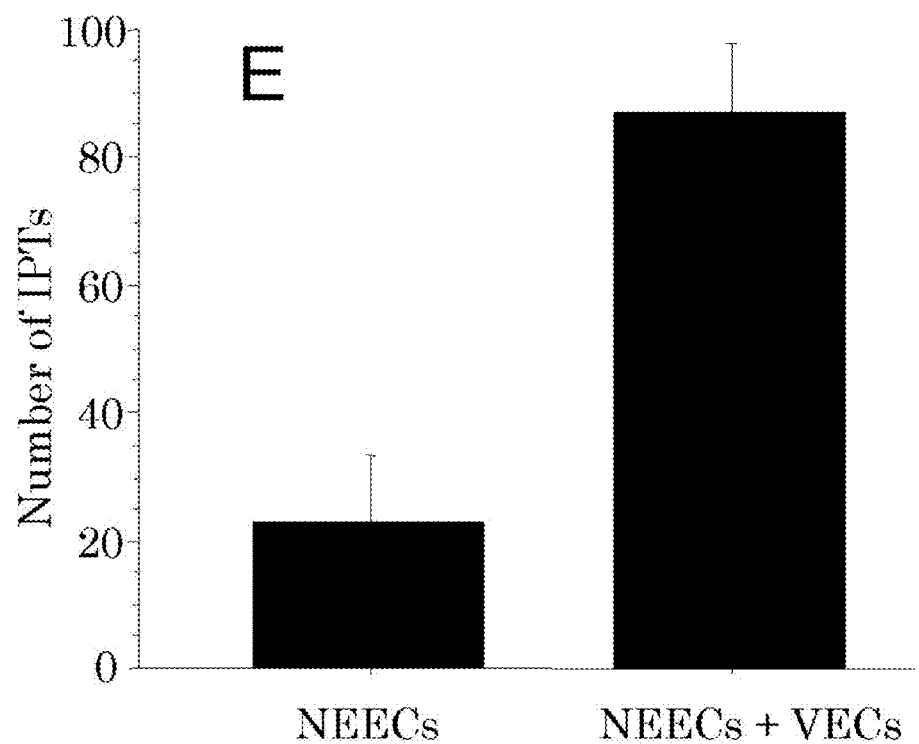
Figures 1, 8:
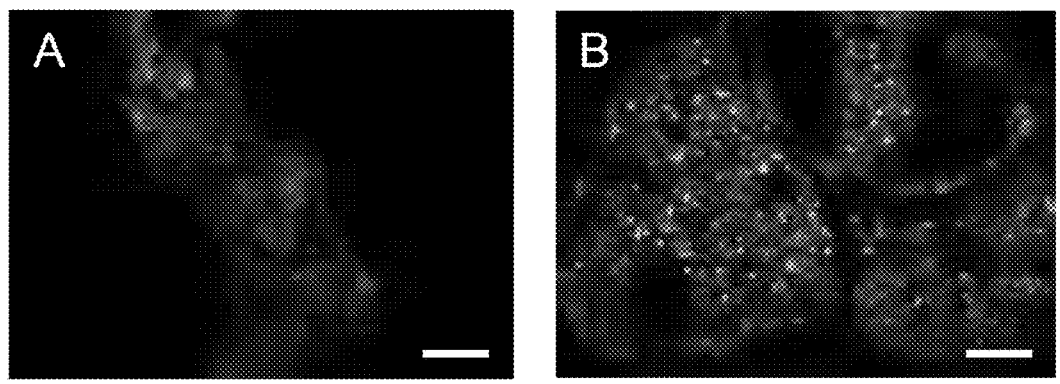
Figures 2, 8:
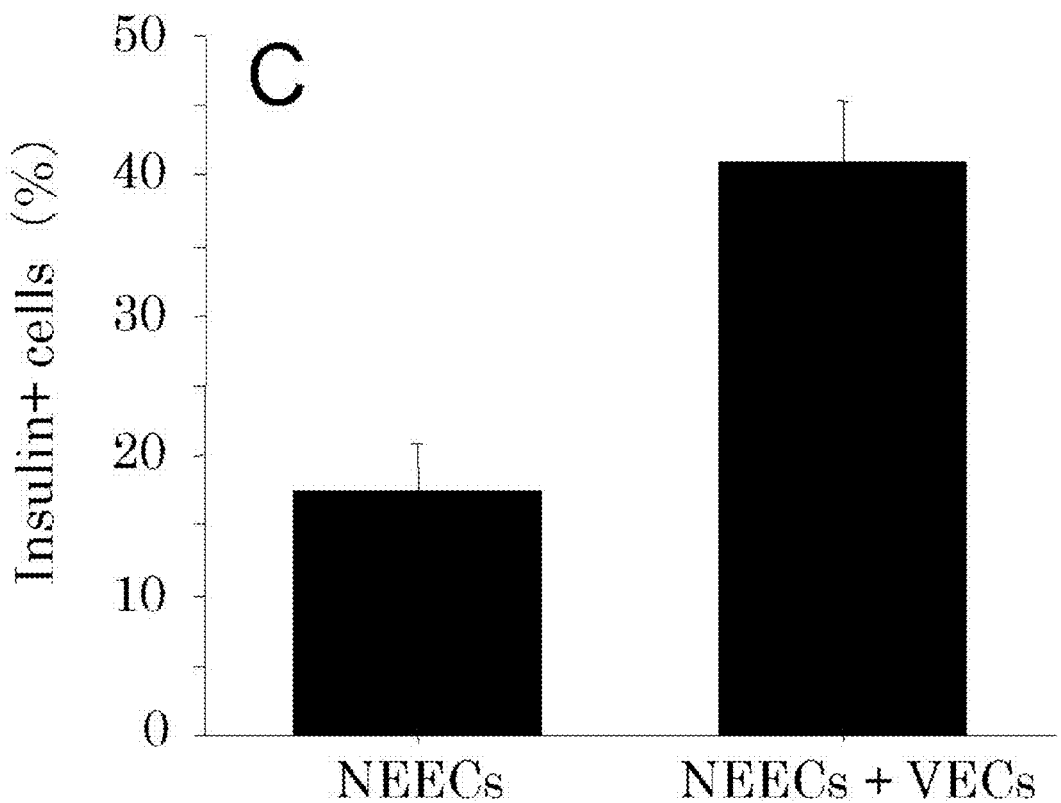

IPTs after the maturation period of EXAMPLE 11 were counted and measured of their diameters, thereby calculated the IEQs to evaluate tissue production. One IEQ equivalent equaled to a spherical tissue (IPT) of about 200 micrometer diameter. This calculation was based on the volume of the IPTs, which was translated to IEQs representing the number of IPTs obtained (FIG. 7-2). The tissues were also evaluated with respect to the relative proportions of insulin-positive cells by standard immunohistochemical procedures. IPTs were fixed in 4% paraformaldehyde in phosphate buffer at 4° C. for 18 hours. Fixed IPTs were washed in PBS at 4° C. for 18 hours, embedded in 2% agarose, dehydrated in alcohol series, cleared in xylene and embedded in paraffin. Four micrometer paraffin sections were de-waxed on glass slides, rehydrated in alcohol series and PBS. The IPT sections were blocked with a blocking solution at RT for 1 hour, and treated with anti-insulin antibody (Millipore International, Inc., Linco 4011-01F)(1:400) at RT for 1 hour, washed with blocking solution and treated with Cy3-conjugated secondary antibody (Anti-Guinea Pig IgG) (1:800). Nuclei were stained with DAPI, and the slides were mounted with VectraShield (Vector Laboratories) and observed under a fluorescent microscope (FIGS. 8-1). For this, four micrometer paraffin sections of IPTs were stained with an anti-insulin antibody and a Cy3-conjugated secondary antibody. Size bars represent 30 micrometer in FIGS. 8-1. The percentage of insulin-positive cells was calculated relative to the number of DAPI-stained nuclei indicating the total number of cells in a given field of observation (FIG. 8-2). As shown in FIG. 8-2, IPTs generated from the tissue complex contained more insulin-positive cells than those of NEECs alone (n=5 representative IPTs for each group, Unpaired t-test, p<0.001). For further comparing IPTs generated from the tissue complex and that from NEECs alone, insulin mRNA expressions amplified by semi-quantitative PCR were measured. FIG. 9A shows thus obtained image, on which M represents DNA size markers and a pattern for native islets is also shown. FIG. 9B shows relative expression intensities for insulin1 (Ins1) (Paired t-test: Ins1, n=5 sample pairs, p<0.0001); and FIG. 9C shows those for insulin2 (Ins2) (Paired t-test: Ins2, n=4 sample pairs, p<0.0001). As seen from the FIGS. 9B and) C, IPTs generated from a tissue complex of NEECs and VECs showed greater relative expression intensities than those for IPTs generated from NEECs alone for both insulin1 (Ins1) and insulin2 (Ins2).

Example 13

Evaluation of Insulin-Secreting Function

Insulin-secreting function was evaluated by a glucose stimulation method. Approximately 20 IEQs of IPTs alter 20 days of maturation (obtained by EXAMPLE 11) were pre-incubated with 200 microliter KREBS ringer solution supplemented with 0.1% BSA, 10 mM Hepes, PenStrep (50/50) and 5 mM D-glucose, a low glucose solution, in a well of a U-shape bottom 96-well plate (Nalgene Nunc International K.K.) at 37° C. and 5% $CO_2$ for one hour. Native 20 IEQs of native islets (BALB/c mouse) were also pre-incubated but for overnight (18 hours) before glucose stimulation in order to acclimate them to the experimental conditions. The KREBS ringer solution was carefully removed, washed 2-3 times and loaded with the same amount of fresh solution, and incubated at 37° C. and 5% $CO_2$ for two hours. After incubation, 150 microliter of the low glucose solution was collected from the wells and stored at −30° C. for later analyses, the IPTs were washed 2-3 times and loaded with the same amount of fresh ringer solution but with 20 mM D-glucose, a high glucose solution, and incubated at 37° C. and 5% $CO_2$ for two hours, followed by collecting 150 micrometer of the high glucose solution from the wells to be stored at −30° C. for later analyses. The collected KREBS ringer solutions were thawed, centrifuged briefly to take 50 microliter from each sample and subjected to C-peptide assay by ELISA (Shibayagi, Co.) (FIG. 10A) or insulin assay by ELISA (Mercodia AB, Uppsala, Sweden) (FIG. 10B) according to the manufacturers' instructions. The tissues were then subjected to RT-PCR as in EXAMPLE 9 to test for Ins1 and Ins2 with which native islets are routinely evaluated of their maturational and functional status (FIGS. 10A, 10B). As shown in FIG. 10A, IPTs generated from a tissue complex of NEECs and VECs showed larger glucose responsiveness in C-peptide secretion when challenged with increased glucose concentrations (Two-way ANOVA: effect=NEECs alone vs. NEECs+VECs, F=19.7, n=5 groups, p=0.0004; effect=low glucose vs. high glucose concentrations, F=5.7, n=5 groups, p=0.0295). Further, as shown in FIG. 10B, IPTs generated from a tissue complex of NEECs and VECs showed the amounts of secreted insulin of 1/10 to 1/2 of those of the native islets (BALB/c mouse), but glucose response of the former was better than that of the latter at least in the experimental conditions used (Two-way ANOVA: effect=IPTs vs. Native islets, F=11797.8, n (IPTs)=4 groups, n (Native islets)=3 groups, p<0.0001; effect=low glucose vs. high glucose concentrations, F=1223.2, p<0.0001).

Example 14

Islet Cell Culture on a Monolayer of VECs

Figures 1, 11:
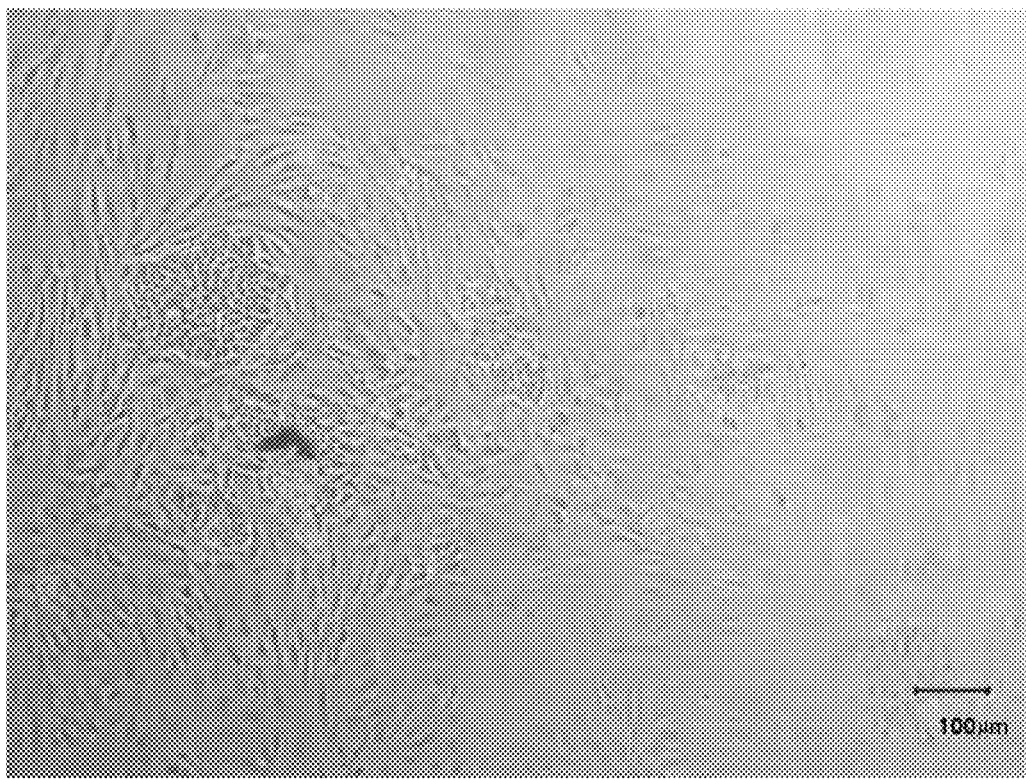
Figures 2, 11:
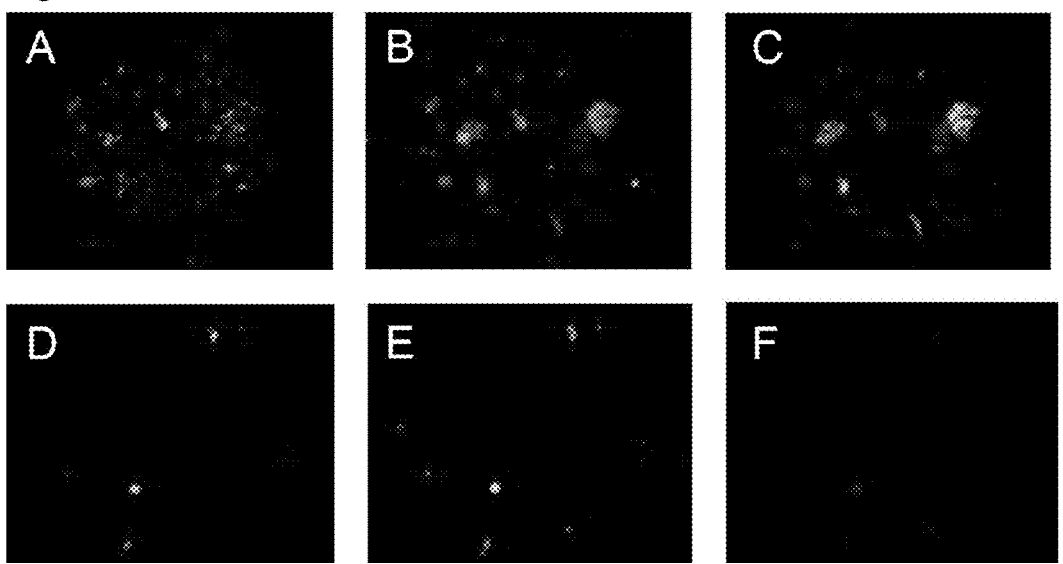
Figure 11:
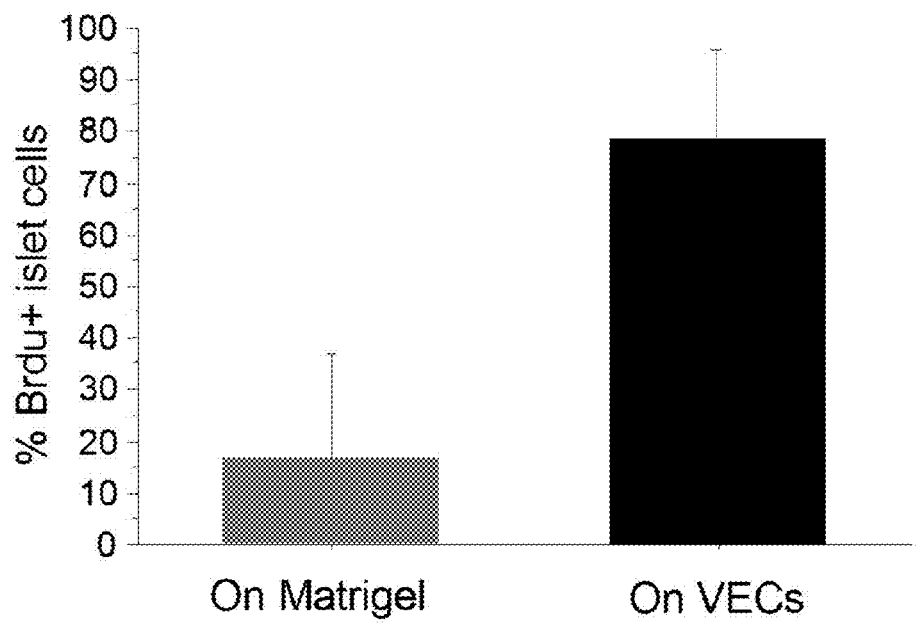
Figure 3:
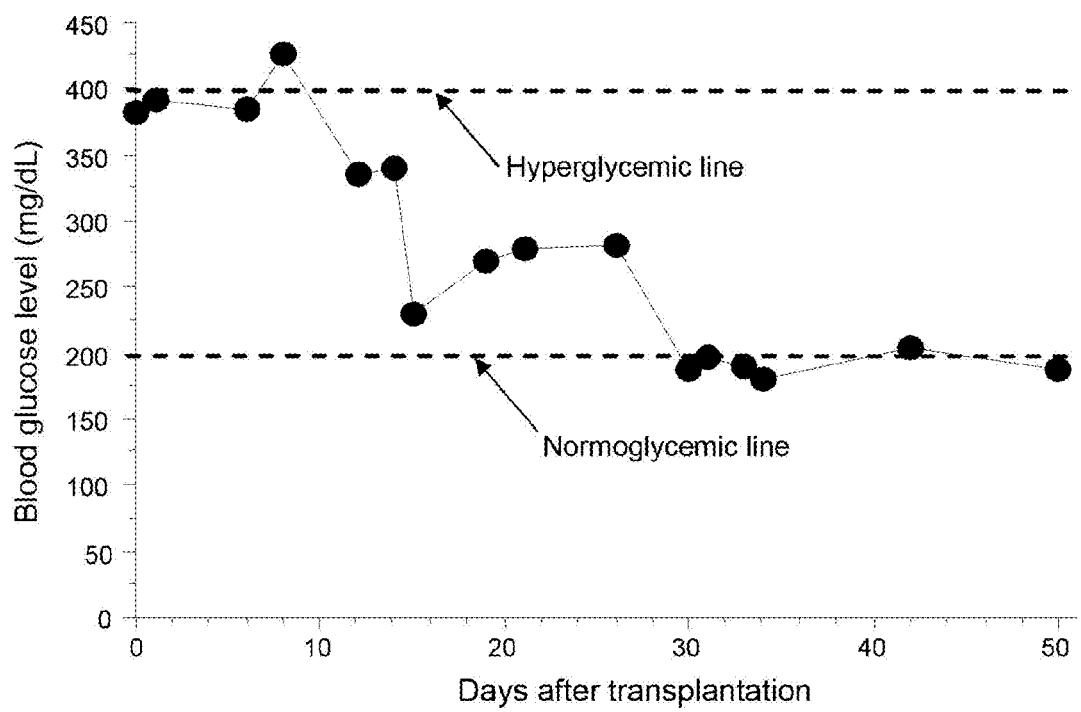

Native islets were isolated from C57Bl/6 mice as described in EXAMPLE 1, islet cells were dissociated by incubating with Accutase at RT for 10 min. These cells were seeded into slide chambers either coated with 0.2 mg/ml growth factor-reduced Matrigel (BD Biosciences) or slide chambers to which VECs obtained by EXAMPLE 10 had been cultured to form a monolayer. The islet cells were cultured in RPMI1640 with 10% FCS and PenStrep (50/50) for 2 days (FIG. 11-1) and were pulsed with 10 micromolar Brdu for the last 30 min. of culture. For immunocytochemistry, they were fixed in 70% ethanol for 30 min at RT, which was followed by the insulin staining procedure as in EXAMPLE 7. After washed with PBS, the cells were stained with anti-Brdu primary antibody (Clone:IIB5, Santa Cruz Biotechnology, Inc.) and secondary antibody (goat anti-mouse IgG-FITC, Santa Cruz Biotechnology, Inc.) at dilution factors of 1:200 and 1:400, respectively. Fluorescent images were observed as in EXAMPLE 7 (FIG. 11-2). FIG. 11-2 shows a series of immunocytochemical images of islet cells seeded on a monolayer of VECs on a chamber slide (A, B and C) and those seeded on a coated surfaces of a chamber slide (D, E and F). For FIGS. 11-2, A and D: DAPI; B and E: anti-insulin-Cy3; C and F: anti-Brdu-FITC. FIG. 11-3 shows a graph indicating that Bromodeoxyuridine positive cells (% Brdu+ cells) was significantly higher for islet cells grown on VECs than Matrigel (Unpaired Student t-test: t=6.57, n=8/group, p<0.0001).

Example 15

In Vivo Functional Evaluation of IPTs

Mice of the same sex and strain at ages between 9 to 14 weeks served as recipients, to which IPTs after the maturation of EXAMPLE 11 were transplanted. Overnight-fasted mice were rendered diabetic by injecting streptozotocin (110-150 mg/kg body weight) intraperitoneally, and blood glucose levels were measured on the 4th day after injection and subsequently once in every 2-5 days. Mice with the blood glucose levels of above 400 mg/dl on two consecutive days were considered as diabetic. The ventro-lateral peritoneum of diabetic mice in anesthesia was surgically opened and transplanted with 700 to 1000 IEQs of IPTs beneath a kidney capsule. The other kidney was left intact. The incision was closed by a double-closure technique before the mice were released from anesthesia. Operated mice were followed up by measuring body weights and blood glucose levels by Accu-Chek Active (Roche Diagnostics, Inc.) for 50 days (FIG. 12A). FIG. 12A shows the changes in blood glucose levels measured for a diabetic mouse into which 700 IEQ's of IPTs generated from the pancreatic tissues of donor mice of the same strain were transplanted under the kidney capsule. Day "0" indicates the day of transplantation. Blood glucose levels above 400 mg/dl and below 200 mg/dl are considered hyperglycemic (diabetic) and normoglycemic (non-diabetic and normal), respectively. The mouse that received the transplant showed decreasing blood glucose levels in the first two weeks. When the kidney with the IPT transplant was analyzed for insulin+ cells by immunohistochemistry in the same manner as performed in EXAMPLE 12, insulin+ cell clusters were clearly visible below the kidney capsule (FIG. 12B).

The invention claimed is:

1. A method of producing insulin-producing tissues (IPTs) by culturing, comprising:
   (a) seeding pancreatic discards, which are left-over tissues remaining after isolation of islets from a postnatal pancreas, in a first culture container or culture substrate to produce floating tissue debris and non-endocrinal epithelial cells (NEECs), wherein said NEECs adhere to the culture container or culture substrate;
   (b) separating said NEECs from said floating tissue debris;
   (c) culturing said separated NEECs in vitro in a first culture medium and isolating said NEECs;
   (d) seeding said separated floating tissue debris into a second culture medium to produce vascular endothelial cells (VECs) and second floating tissue debris;
   (e) separating said vascular endothelial cells (VECs) from said second floating tissue debris;
   (f) culturing said separated VECs in vitro in a third culture medium and isolating said VECs;
   (g) mixing said isolated NEECs and said isolated VECs; and
   (h) generating, in vitro, a tissue complex comprising the mixture of said isolated NEECs and said isolated VECs.

2. The method according to claim 1, wherein the culture container for seeding said pancreatic discards comprises a first serum-containing culture medium and wherein said first culture container for seeding said pancreatic discards is coated with collagen or other cell-adhesion materials.

3. The method according to claim 1, wherein said culturing of said separated NEECs is performed until the emergence of clonal colonies of said separated NEECs with sizes ranging from 10-30 micrometer in diameter; and wherein the first culture medium is a serum-free medium.

4. The method according to claim 3, wherein said serum-free medium contains keratinocyte growth factor (KGF) and, optionally, insulin-transferrin-sodium selenite supplement or other growth factor supplements.

5. The method according to claim 1, wherein the first culture medium contains serum; and wherein step (c) further includes replacing said first culture medium during said separated NEEC culturing with a first serum-free medium containing an insulin-transferrin-sodium selenite supplement and continuing the culture; and then replacing said first serum-free medium with a second serum-free medium.

6. The method according to claim 3, further comprising:
(1) treating said clonal colonies with a first tissue-dissociation enzyme solution upon or after said emergence to dissociate said colonies from the first culture container, filtering and/or centrifuging said clonal colonies, and removing said clonal colonies from the serum-free medium; wherein after the removal of the clonal colonies, there are left-over cells (LOCs) that remain on the first culture container that are not removed with tissue-dissociation enzyme solution; and
(2) culturing said removed colonies in a second culture container that is coated with collagen or other cell adhesion materials in a second serum-free medium.

7. The method according to claim 6, wherein the collagen or other cell adhesion materials contain Rho-associated coiled-coil containing protein kinase (Rock) inhibitor, epidermal growth factor (EGF), and hepatocyte growth factor (HGF).

8. The method according to claim 6, wherein the second serum-free medium is supplemented with atorvastatin.

9. The method according to claim 6, further comprising culturing said LOCs in said first culture container.

10. The method according to claim 6, further comprising detaching said LOCs from said first culture container with a second tissue-dissociation enzyme solution.

11. The method according to claim 6, wherein said second serum-free medium contains proliferation-enhancing paracrine factors from said LOCs.

12. The method according to claim 1, wherein step (d) further comprises:
(d2) seeding said separated floating tissue debris into said second culture medium on a second culture container or culture substrate that is coated with collagen or other cell adhesion materials; and
(d3) expanding the VECs in the floating tissue debris subsequent to said seeding;
wherein said second culture medium contains serum.

13. The method according to claim 12, wherein step (e) further comprises:
(e2) replenishing said second culture medium with a serum-containing culture medium;
(e3) removing non-adherent cells and tissues during said replenishing; and
(e4) purifying the VECs by antibody binding to produce separated VECs.

14. The method according to claim 13, wherein said culturing of said separated VECs in vitro in a third culture medium of step (f) further comprises:
(f2) seeding said separated VECs into the third culture medium; and
(f3) replenishing said third culture medium.

15. The method according to claim 1, wherein step (g) further comprises:
(g2) treating said isolated NEECs and said isolated VECs with a tissue-dissociation enzyme solution;
(g3) centrifuging said treated NEECs and said treated VECs;
(g4) removing said centrifuged NEECs and said centrifuged VECs from said first culture medium and said third culture medium, respectively; and
(g5) placing said removed NEECs and said removed VECs into a low adherence culture container with a serum-containing differentiation culture medium.

16. The method according to claim 15, wherein step (h) further comprises:
(h2) swirling said low adherence culture container to form an initial tissue complex;
(h3) placing the low adherence culture container horizontally, without motion;
(h4) replenishing said serum-containing differentiation culture medium, thereby maturing said IPTs.

17. The method according to claim 16, wherein said serum-containing differentiation culture medium contains activin, growth factors, bone morphogenetic protein, and $CaCl_2$;
wherein a mixing ratio of said removed NEECs and said removed VECs is in a range from 3% to 25%, wherein said mixing ratio is obtained by dividing the cell number of the removed VECs by a sum of the cell numbers of said removed NEECs and said removed VECs; and
wherein $CaCl_2$ is omitted from said serum-containing differentiation culture medium upon said maturation of IPTs.

18. A method of producing insulin-producing tissues by culturing, comprising:
(a) treating a postnatal pancreas to produce natural islet cells and pancreatic discards;
(b) seeding said pancreatic discards in a first culture container or culture substrate to produce floating tissue debris and non-endocrinal epithelial cells (NEECs), wherein said NEECs adhere to the culture container or culture substrate;
(c) separating said NEECs from said floating tissue debris;
(d) seeding said floating tissue debris into a culture medium to produce vascular endothelial cells (VECs) and second floating tissue debris;
(e) separating said VECs from said second floating tissue debris;
(f) culturing said separated VECs in vitro to produce isolated VECs;
(g) culturing said isolated VECs in vitro in a manner to form a VEC monolayer;
(h) seeding and growing said natural islet cells on said VEC monolayer.

19. The method according to claim 18, wherein step (f) further comprises:
(f2) seeding and expanding said separated VECs on a second culture container or culture substrate that is coated with collagen or other cell adhesion materials to produce expanded VECs;
(f3) removing said expanded VECs from said second culture container or culture substrate; and
(f4) purifying said removed VECs by antibody binding to produce said isolated VECs.

* * * * *